US009770705B2

(12) United States Patent
Murphy et al.

(10) Patent No.: US 9,770,705 B2
(45) Date of Patent: Sep. 26, 2017

(54) OXIDATION CATALYSTS

(75) Inventors: Vincent J. Murphy, San Jose, CA (US); James Shoemaker, Gilroy, CA (US); Guang Zhu, Foster City, CA (US); Raymond Archer, Sunnyvale, CA (US); George Frederick Salem, Los Altos, CA (US); Eric L. Dias, Belmont, CA (US)

(73) Assignee: Rennovia Inc., Santa Clara, CA (US)

( * ) Notice: Subject to any disclaimer, the term of this patent is extended or adjusted under 35 U.S.C. 154(b) by 445 days.

(21) Appl. No.: 12/966,702

(22) Filed: Dec. 13, 2010

(65) Prior Publication Data

US 2011/0306790 A1    Dec. 15, 2011

Related U.S. Application Data

(63) Continuation-in-part of application No. 12/814,188, filed on Jun. 11, 2010.

(51) Int. Cl.
*B01J 23/42* (2006.01)
*B01J 23/52* (2006.01)
(Continued)

(52) U.S. Cl.
CPC ............ *B01J 23/52* (2013.01); *B01J 21/063* (2013.01); *B01J 21/066* (2013.01); *B01J 21/08* (2013.01);
(Continued)

(58) Field of Classification Search
CPC ... C07C 51/235; C07C 253/00; C07C 209/00; C08G 69/36; C08G 63/16; C07D 309/30; C07D 223/10; C07D 201/08
See application file for complete search history.

(56) References Cited

U.S. PATENT DOCUMENTS

| 2,472,168 A | 6/1949 | Mehltretter et al. |
| 2,750,394 A | 6/1956 | Peniston |

(Continued)

FOREIGN PATENT DOCUMENTS

| CA | 2097812 A1 | 6/1992 |
| CN | 101486639 | 7/2009 |

(Continued)

OTHER PUBLICATIONS

Prati et al, "Effect of gold addition on Pt and Pd catalysts in liquid phase oxidations", Topics in Catalysis vol. 44, Nos. 1-2, Jun. 2007, 319-324.*

(Continued)

*Primary Examiner* — Melvin C Mayes
*Assistant Examiner* — James Corno
(74) *Attorney, Agent, or Firm* — Senniger Powers LLP

(57) ABSTRACT

Disclosed are catalysts comprised of platinum and gold. The catalysts are generally useful for the selective oxidation of compositions comprised of a primary alcohol group and at least one secondary alcohol group wherein at least the primary alcohol group is converted to a carboxyl group. More particularly, the catalysts are supported catalysts including particles comprising gold and particles comprising platinum, wherein the molar ratio of platinum to gold is in the range of about 100:1 to about 1:4, the platinum is essentially present as Pt(0) and the platinum-containing particles are of a size in the range of about 2 to about 50 nm. Also disclosed are methods for the oxidative chemocatalytic conversion of carbohydrates to carboxylic acids or derivatives thereof. Additionally, methods are disclosed for the selective oxidation of glucose to glucaric acid or derivatives thereof using catalysts comprising platinum and gold. Further, methods are disclosed for the production of such catalysts.

22 Claims, 2 Drawing Sheets

(51) Int. Cl.
| | | |
|---|---|---|
| *C07C 51/235* | (2006.01) | |
| *C07C 51/377* | (2006.01) | |
| *C07C 51/41* | (2006.01) | |
| *C07C 209/00* | (2006.01) | |
| *C07C 253/00* | (2006.01) | |
| *C07D 201/08* | (2006.01) | |
| *C07D 223/10* | (2006.01) | |
| *C07D 309/30* | (2006.01) | |
| *C08G 63/16* | (2006.01) | |
| *C08G 69/14* | (2006.01) | |
| *C08G 69/26* | (2006.01) | |
| *C08G 69/36* | (2006.01) | |
| *B01J 21/06* | (2006.01) | |
| *B01J 21/08* | (2006.01) | |
| *B01J 29/06* | (2006.01) | |
| *B01J 35/00* | (2006.01) | |
| *B01J 37/02* | (2006.01) | |
| *B01J 37/18* | (2006.01) | |

(52) U.S. Cl.
CPC ............ *B01J 23/42* (2013.01); *B01J 29/06* (2013.01); *B01J 35/0006* (2013.01); *B01J 35/0013* (2013.01); *B01J 37/0211* (2013.01); *B01J 37/0236* (2013.01); *B01J 37/0248* (2013.01); *B01J 37/18* (2013.01); *C07C 51/235* (2013.01); *C07C 51/377* (2013.01); *C07C 51/412* (2013.01); *C07C 209/00* (2013.01); *C07C 253/00* (2013.01); *C07D 201/08* (2013.01); *C07D 223/10* (2013.01); *C07D 309/30* (2013.01); *C08G 63/16* (2013.01); *C08G 69/14* (2013.01); *C08G 69/26* (2013.01); *C08G 69/36* (2013.01); *C07B 2200/07* (2013.01); *Y02P 20/582* (2015.11)

(56) References Cited

U.S. PATENT DOCUMENTS

| | | |
|---|---|---|
| 2,851,468 A | 9/1958 | Snyder |
| 2,917,520 A | 12/1959 | Cope |
| 2,929,823 A | 3/1960 | Garber et al. |
| 3,070,633 A | 12/1962 | Utne et al. |
| 3,083,236 A | 3/1963 | Utne et al. |
| 3,118,912 A | 1/1964 | Smith |
| 3,189,651 A | 6/1965 | Garber et al. |
| 3,225,066 A | 12/1965 | Baak |
| 3,326,944 A | 6/1967 | Baak |
| 3,483,228 A | 12/1969 | Garber et al. |
| 3,607,922 A | 9/1971 | Acres et al. |
| 3,671,566 A | 6/1972 | Decker et al. |
| 3,761,579 A | 9/1973 | Curtis, Jr. et al. |
| 3,860,626 A | 1/1975 | Putnin et al. |
| 3,873,614 A | 3/1975 | Lamberti et al. |
| 3,896,056 A | 7/1975 | Benjamin et al. |
| 3,917,707 A | 11/1975 | Williams et al. |
| 4,060,547 A | 11/1977 | Paulik et al. |
| 4,067,900 A | 1/1978 | Intilli |
| 4,078,139 A | 3/1978 | Barton et al. |
| 4,302,432 A | 11/1981 | Polichnowski |
| 4,337,202 A | 6/1982 | Hearon et al. |
| 4,339,387 A | 7/1982 | Fleche et al. |
| 4,363,815 A | 12/1982 | Yu et al. |
| 4,400,468 A | 8/1983 | Faber |
| 4,401,823 A | 8/1983 | Arena |
| 4,439,551 A | 3/1984 | Yeakey et al. |
| 4,533,743 A | 8/1985 | Medeiros et al. |
| 4,590,283 A | 5/1986 | Gaset et al. |
| 4,605,790 A | 8/1986 | Wojtkowski |
| 4,722,997 A | 2/1988 | Roerdink et al. |
| 4,740,605 A | 4/1988 | Rapp |
| 4,767,856 A | 8/1988 | Dockner et al. |
| 4,820,880 A | 4/1989 | Urbas |
| 4,833,230 A | 5/1989 | Kiely et al. |
| 4,843,173 A | 6/1989 | Saito et al. |
| 4,845,208 A | 7/1989 | Fuertes et al. |
| 4,900,407 A | 2/1990 | Saito et al. |
| 4,912,237 A | 3/1990 | Zeitsch |
| 4,971,657 A | 11/1990 | Avignon et al. |
| 4,977,283 A | 12/1990 | Leupold et al. |
| 5,071,754 A | 12/1991 | Walkup et al. |
| 5,132,452 A | 7/1992 | Deller et al. |
| 5,132,456 A | 7/1992 | King et al. |
| 5,149,680 A | 9/1992 | Kitson et al. |
| 5,196,617 A | 3/1993 | Kovenklioglu et al. |
| 5,247,012 A | 9/1993 | Vyvoda |
| 5,252,473 A | 10/1993 | Walkup et al. |
| 5,264,624 A | 11/1993 | Vogtel et al. |
| 5,276,240 A | 1/1994 | Timmons et al. |
| 5,281,647 A | 1/1994 | Eapen |
| 5,290,852 A | 3/1994 | Vyvoda |
| 5,359,137 A | 10/1994 | Burke |
| 5,426,219 A | 6/1995 | Lehnhardt et al. |
| 5,426,252 A | 6/1995 | Sherif |
| 5,430,214 A | 7/1995 | Smith et al. |
| 5,434,233 A | 7/1995 | Kiely et al. |
| 5,484,914 A | 1/1996 | Skibida et al. |
| 5,487,987 A | 1/1996 | Frost et al. |
| 5,516,960 A | 5/1996 | Robinson |
| 5,562,777 A | 10/1996 | Farone et al. |
| 5,599,977 A | 2/1997 | Kiely et al. |
| 5,616,496 A | 4/1997 | Frost et al. |
| 5,625,110 A | 4/1997 | Schoedel et al. |
| 5,683,952 A | 11/1997 | Onozawa et al. |
| 5,689,000 A | 11/1997 | Ebner et al. |
| 5,721,189 A | 2/1998 | Zhang |
| 5,726,046 A | 3/1998 | Farone et al. |
| 5,731,467 A | 3/1998 | Fleche |
| 5,766,439 A | 6/1998 | Eyal et al. |
| 5,772,013 A | 6/1998 | Kunz et al. |
| 5,773,677 A | 6/1998 | Lansink-Rotgerink et al. |
| 5,789,333 A | 8/1998 | Angelici et al. |
| 5,811,628 A | 9/1998 | Weber et al. |
| 5,820,687 A | 10/1998 | Farone et al. |
| 5,900,511 A | 5/1999 | Sengupta et al. |
| 5,919,994 A | 7/1999 | Rao |
| 5,922,635 A | 7/1999 | Olah et al. |
| 5,981,420 A | 11/1999 | Nakano et al. |
| 5,986,127 A | 11/1999 | Ionkin et al. |
| 5,998,657 A | 12/1999 | Gogate et al. |
| 6,008,418 A | 12/1999 | Baur et al. |
| 6,028,025 A | 2/2000 | Ying et al. |
| 6,049,004 A | 4/2000 | Kiely et al. |
| 6,087,296 A | 7/2000 | Harper |
| 6,127,585 A | 10/2000 | Duzick et al. |
| 6,147,027 A | 11/2000 | Miyake et al. |
| 6,147,208 A | 11/2000 | Achhammer et al. |
| 6,180,830 B1 | 1/2001 | Jacquot |
| 6,228,800 B1 | 5/2001 | Yamaguchi et al. |
| 6,232,264 B1 | 5/2001 | Lukehart et al. |
| 6,391,821 B1 | 5/2002 | Satoh et al. |
| 6,403,521 B1 | 6/2002 | Ishii et al. |
| 6,436,866 B1 | 8/2002 | Nishikido et al. |
| 6,437,206 B1* | 8/2002 | Meyer et al. ................ 585/260 |
| 6,441,202 B1 | 8/2002 | Lightner |
| 6,444,608 B1 | 9/2002 | Oki et al. |
| 6,462,220 B1 | 10/2002 | Luyken et al. |
| 6,476,260 B1 | 11/2002 | Herrmann et al. |
| 6,495,730 B1 | 12/2002 | Konishi et al. |
| 6,498,269 B1 | 12/2002 | Merbouh et al. |
| 6,500,649 B2 | 12/2002 | Fouache et al. |
| 6,518,440 B2 | 2/2003 | Lightner |
| 6,521,779 B1 | 2/2003 | Boschat et al. |
| 6,559,275 B2 | 5/2003 | Minami et al. |
| 6,569,670 B2 | 5/2003 | Anderson et al. |
| 6,569,802 B1 | 5/2003 | Ionkin |
| 6,692,578 B2 | 2/2004 | Schmidt et al. |
| 6,716,339 B2 | 4/2004 | Liu et al. |
| 6,743,928 B1 | 6/2004 | Zeitsch |
| 6,773,512 B2 | 8/2004 | Ennelin et al. |
| 6,861,387 B2 | 3/2005 | Ruth et al. |
| 6,894,135 B2 | 5/2005 | Kiely et al. |

(56) References Cited

U.S. PATENT DOCUMENTS

| | | |
|---|---|---|
| 6,894,160 B2 | 5/2005 | Capan et al. |
| 6,897,338 B2 | 5/2005 | Zhong et al. |
| 6,953,873 B2 | 10/2005 | Cortright et al. |
| 6,958,405 B2 | 10/2005 | Le-Khac et al. |
| 7,084,090 B2 | 8/2006 | Ishii et al. |
| 7,109,145 B2 | 9/2006 | Ruth et al. |
| 7,115,541 B2 | 10/2006 | Ishii et al. |
| 7,138,035 B2 | 11/2006 | Cui et al. |
| 7,161,005 B2 | 1/2007 | Schlingloff et al. |
| 7,166,743 B2 | 1/2007 | Zhong et al. |
| 7,179,366 B2 | 2/2007 | Harle et al. |
| 7,208,439 B2 | 4/2007 | Zhong et al. |
| 7,317,116 B2 | 1/2008 | Sanborn |
| 7,344,696 B2 | 3/2008 | Canos et al. |
| 7,354,743 B2 | 4/2008 | Vlasenko et al. |
| 7,364,880 B2 | 4/2008 | Ray et al. |
| 7,371,894 B2 | 5/2008 | Wonders et al. |
| 7,385,081 B1 | 6/2008 | Gong |
| 7,393,676 B2 | 7/2008 | Gokarn et al. |
| 7,399,855 B2 | 7/2008 | Frost |
| 7,411,078 B2 | 8/2008 | Miura et al. |
| 7,413,882 B2 | 8/2008 | Berka et al. |
| 7,432,382 B2 | 10/2008 | Sanborn et al. |
| 7,459,597 B2 | 12/2008 | Koivusalmi et al. |
| 7,517,675 B2 | 4/2009 | Vercauteren et al. |
| 7,572,925 B2 | 8/2009 | Dumesic et al. |
| 7,579,489 B2 | 8/2009 | Sanborn |
| 7,579,490 B2 | 8/2009 | Sanborn et al. |
| 7,582,444 B2 | 9/2009 | Hughes |
| 7,608,689 B2 | 10/2009 | Harris et al. |
| 8,038,763 B2 | 10/2011 | Eichhorn et al. |
| 8,568,680 B2 | 10/2013 | Hui et al. |
| 9,023,751 B2 | 5/2015 | Mizutani |
| 2002/0111458 A1 | 8/2002 | Minami et al. |
| 2003/0015457 A1 | 1/2003 | Liu et al. |
| 2005/0009694 A1* | 1/2005 | Watts et al. .......... 502/304 |
| 2005/0233423 A1 | 10/2005 | Berka et al. |
| 2005/0272134 A1 | 12/2005 | Hughes |
| 2006/0084800 A1 | 4/2006 | Chenault |
| 2006/0084817 A1 | 4/2006 | Chenault |
| 2007/0027341 A1* | 2/2007 | Rossi .......... B01J 23/52 562/525 |
| 2007/0031918 A1 | 2/2007 | Dunson, Jr. et al. |
| 2007/0031919 A1 | 2/2007 | Dunson, Jr. et al. |
| 2007/0111294 A1 | 5/2007 | Burgard et al. |
| 2007/0166220 A1* | 7/2007 | Ceyer et al. .......... 423/437.2 |
| 2007/0193960 A1 | 8/2007 | Frank et al. |
| 2007/0215484 A1 | 9/2007 | Peterson et al. |
| 2007/0219397 A1 | 9/2007 | Holladay et al. |
| 2007/0287845 A1 | 12/2007 | Lilga et al. |
| 2008/0033187 A1 | 2/2008 | Zhao et al. |
| 2008/0033188 A1 | 2/2008 | Dumesic et al. |
| 2008/0033205 A1 | 2/2008 | Kiely et al. |
| 2008/0041366 A1 | 2/2008 | Wahnon |
| 2008/0096242 A1 | 4/2008 | Sanders et al. |
| 2008/0103232 A1 | 5/2008 | Lake et al. |
| 2008/0103318 A1 | 5/2008 | Lilga et al. |
| 2008/0103340 A1 | 5/2008 | Binder et al. |
| 2008/0206562 A1* | 8/2008 | Stucky et al. .......... 428/403 |
| 2008/0216391 A1 | 9/2008 | Cortright et al. |
| 2008/0293109 A1 | 11/2008 | Berka et al. |
| 2008/0300434 A1 | 12/2008 | Cortright et al. |
| 2008/0300435 A1 | 12/2008 | Cortright et al. |
| 2009/0018300 A1 | 1/2009 | Bloom et al. |
| 2009/0047719 A1 | 2/2009 | Burgard et al. |
| 2009/0131259 A1 | 5/2009 | Kiely et al. |
| 2009/0171037 A1 | 7/2009 | Aoshima et al. |
| 2009/0211942 A1 | 8/2009 | Cortright et al. |
| 2009/0215128 A1 | 8/2009 | Vlasenko et al. |
| 2009/0250653 A1 | 10/2009 | Kiely et al. |
| 2009/0255171 A1 | 10/2009 | Dumesic et al. |
| 2009/0270245 A1 | 10/2009 | Kumar et al. |
| 2009/0305364 A1 | 12/2009 | Burgard et al. |
| 2010/0113263 A1* | 5/2010 | Lee et al. .......... 502/304 |
| 2010/0196802 A1 | 8/2010 | Tabata et al. |
| 2011/0144385 A1 | 6/2011 | Franke et al. |
| 2012/0123138 A1* | 5/2012 | Ganhy et al. .......... 552/265 |

FOREIGN PATENT DOCUMENTS

| | | |
|---|---|---|
| CN | 101695657 A | 4/2010 |
| DE | 19609069 A1 | 9/1997 |
| EP | 0096913 A1 | 12/1983 |
| EP | 0151498 A2 | 8/1986 |
| EP | 1728844 A1 | 12/2006 |
| EP | 2033958 A1 | 3/2009 |
| FR | 2556344 A1 | 6/1985 |
| FR | 2663933 A1 | 1/1992 |
| FR | 2664273 A1 | 1/1992 |
| FR | 2669635 A1 | 5/1992 |
| GB | 591858 | 9/1947 |
| GB | 600871 | 4/1948 |
| GB | 876463 | 9/1961 |
| GB | 1044883 | 10/1966 |
| JP | 33-7620 | 8/1958 |
| JP | 53-144506 | 12/1978 |
| JP | 55-013243 | 1/1980 |
| JP | 59-190984 | 10/1984 |
| JP | 2-088569 A | 3/1990 |
| JP | 10-216518 A | 8/1998 |
| JP | 2001-316311 A | 11/2001 |
| JP | 2002-308819 A | 10/2002 |
| JP | 2005-060447 A | 3/2005 |
| JP | 2005154302 A | 6/2005 |
| JP | 2005-200321 A | 7/2005 |
| JP | 2005-232116 A | 9/2005 |
| JP | 2007-145736 A | 6/2007 |
| LV | 10857 B | 8/1996 |
| WO | 8201701 A1 | 5/1982 |
| WO | 9421690 A2 | 9/1994 |
| WO | 9507996 A1 | 3/1995 |
| WO | 9604224 A1 | 2/1996 |
| WO | 9638402 A1 | 12/1996 |
| WO | 2005003072 A1 | 1/2005 |
| WO | 2006005070 A1 | 1/2006 |
| WO | 2006100584 A2 | 9/2006 |
| WO | 2006119357 A2 | 11/2006 |
| WO | 2007075370 A2 | 7/2007 |
| WO | 2007075476 A2 | 7/2007 |
| WO | 2007089677 A2 | 8/2007 |
| WO | 2007141293 A1 | 12/2007 |
| WO | 2008021054 A2 | 2/2008 |
| WO | 2008070762 A1 | 6/2008 |
| WO | 2008109877 A1 | 9/2008 |
| WO | 2008144514 A2 | 11/2008 |

OTHER PUBLICATIONS

Soto et al, "Structure-Sensitivity of propylene hydrogenation over cluster-derived bimetallic Pt—Au catalysts", Catalysis Letters vol. 107, Nos. 1-2, Feb. 2006, 319-324.*

Del Angel et al, "Aggregation State of Pt—Au/C Bimetallic Catalysts Prepared by Surface Redox Reactions," Langmuir 16(18), pp. 7210-7217, Aug. 2000.*

Srinivas et al, "Influence of Particle Size and Interaction with the Support on Redox and Catalytic Properties of Metals, Metal Oxides, and Metal Complexes," Nanotechnology in Catalysis vol. 3, pp. 183-220, Dec. 2006.*

Luo et al, "Activity-composition correlation of AuPt alloy nanoparticle catalysts in electrocatalytic reduction of oxygen," Electrochemistry Communications 8(4), pp. 581-587, Apr. 2006.*

Yano et al, "Oxygen Reduction Activity of Carbon-Supported Pt—M (M=V, Ni, Cr, Co, and Fe) Alloys Prepared by Nanocapsule Method," Langmuir 23(11), pp. 6438-6445, Apr. 2007.*

Xiong et al, "Synthesis and characterization of carbon supported PtW catalysts from carbonyl complexes for oxygen electroreduction," Electrochemistry Communications 8(10), pp. 1671-1676, Oct. 2006.*

Prati et al, "Effect of gold addition on Pt and Pd catalysts in liquid phase oxidations," Topics in Catalysis 44(1-2), pp. 319-324, Jun. 2007.*

(56) References Cited

OTHER PUBLICATIONS

Vazquez-Zavala et al., "Study of the structure and selectivity of Pt—Au catalysts supported on Al2O3, TiO2, and SiO2," Applied Surface Science 167(3-4), pp. 177-183, Oct. 2000.*

Somorjai et al., "Colloid Science of Metal Nanoparticle Catalysts in 2D and 3D Structures. Challenges of Nucleation, Growth, Composition, Particle Shape, Size Control and Their Influence on Activity and Selectivity," Topics in Catalysis 49, pp. 126-135, Jun. 2008.*

Benvenutti et al., "FTIR Study of Hydrogen and Carbon Monoxide Adsorption on Pt/TiO2, Pt/ZrO2, and Pt/Al2O3," Langmuir 15(23), pp. 8140-8146, Sep. 1999.*

Sen et al., "The influence of platinum crystallite size on H2 and CO heats of adsorption and CO hydrogenation," Journal of Catalysis 130(1), pp. 9-20, Jul. 1991.*

Gebhardt et al., "A special type of raney-alloy catalyst used in compact biofuel cells," Journal of Applied Electrochemistry 6(2), pp. 127-134, Mar. 1976.*

Kouremenos, K.A., et al., Metabolic Profiling of Infant Urine Using Comprehensive Two-Dimensional Gas Chromatography: Application to the Diagnosis of Organic Acidurias and Biomarker Discovery, 2010, J Chromotography A, 1217:104-111.

Satoh, S., et al., "Electrochemical Reductive Cyclization of Dimethyl Dibromoalkanedioates," 1980, Hok Kaido Dai gaku Kogakubu KenKyu Hokoku, 102:33.

Abstract of CN 1651391 A, Univ Tianjin, 2005, 6 pages.

Jianhua Xu, "The Technological Progress and Market Analysis of Adipic Acid", Chemical Intermediate, No. 6, pp. 4-9, Jun. 30, 2006, Abstract Only, 3 pages.

Yuan MA et al., "Comparison of Production Process of Adiponitrile", Henan Chemical Industry, vol. 24, No. 8, pp. 4-6, Dec. 31, 2007, Abstract Only, 1 pages.

Zhang et al., "Synthesis of Au/Pt bimetallic nanoparticles with a Pt-rich shell and their high catalytic activities for aerobic glucose oxidation," Journal of Colloid and Interface Science 394 (2013) 166-176 (with Appendix A).

Biella, S., et al., "Selective Oxidation of D-Glucose on Gold Catalyst," 2001, Journal of Catalysis, 206, 242-247, 6 pages.

Golunski, S., "Why Use Platinum in Catalytic Converters?" 2007, Platinum Metals Rev. 51/3:162, 1 pages.

Wanjala, B.N., et al., "Gold-Platinum Nanoparticles: Alloy and Hhase Segregation," 2011, J. Mater. Chem., 21:4012-4020, 9 pages.

Preparation of Solid Catalysts, Section 4.8, Spreading and Wetting, G. Ertl, H. Knozinger and J. Weitkamp (editors), Wiley-VCH 1999, pp. 501-526, 36 pages.

Abbadi, A., et al., "Effect of pH in the Pt-Catalyzed Oxidation of D-Glucose to D-Gluconic Acid," 1995, J. Mol. Catal. A: Chem., 97:111-118.

Abbadi, A., et al., "Highly Selective Oxidation of Aldonic Acids to 2-Keto-Aldonic Acids Over Pt—Bi and Pt—Pb Catalysts," 1995, App. Catal. A: General, 124:409-417.

Blanc, B., et al., "Starch-Derived Polyols for Polymer Technologies: Preparation by Hydrogenolysis on Metal Catalysts," Apr. 2000, Green Chemistry, pp. 89-91.

Brown, J.M., Equilibration of D-Glucaric Acid in Aqueous Solution, 2007, Thesis, University of Waikato, 191 pages.

Dirkx, J., et al., "The Oxidation of Glucose with Platinum on Carbon as Catalyst," 1981, J. Catal., 67:1-13.

Dirkx, J., et al., "The Oxidation of Gluconic Acid with Platinum on Carbon as Catalyst," 1981, J. Catal., 67:14-20.

Gehret, T. et al., "Convenient Large-Scale Synthesis of D-Glucaro-1,4:6,3-dilactone," 2009, J. Org. Chem., 74 (21), pp. 8373-8376.

Koso, S., et al., "Chemoselective Hydrogenolysis of Tetrahydrofurfuryl Alcohol to 1,5-Pentanediol," 2009, Chem. Commun., 2035-2037.

Koso, S., et al., "Promoting Effect of Mo on the Hydrogenolysis of Tetrahydrofurfuryl Alcohol to 1,5-pentanediol Over Rh/SiO2," 2009, J. Catal., 267:89-92.

Abstract of BG 100407, Episucres SA, 1997, 1 page.

Saha, B.C., "Hemicellulose Bioconversion," J. Ind. Microbiol. Biotechnol., 2003, 30:279-291.

Venema, F., et al., "Platinum-Catalyzed Oxidation of Aldopentoses to Aldaric Acids," 1992, J. Mol. Catal., 77:75-85.

Wang, T., et al., "Aqueous-Phase Aerobic Oxidation of Alcohols by Soluble Pt Nanoclusters in the Absence of Base," 2007, Chem. Commun., 4375-4377.

Wang T., et al., "Base-free Aqueous-Phase Oxidation of Non-Activated Alcohols with Molecular Oxygen on Soluble Pt Nanoparticles," 2009, Green Chem, 11:562-568.

Besson, M., et al., "Oxidation of Glucose and Gluconate on Pt, Pt Bi, and Pt Au Catalysts," 1996, Recueil des Travaux chimiques des pays-Bas, 115:217-221.

De La Motte, H., "Ueber die Einwirkung von Phosphorpentachlorid und Jodwasserstoffsaure auf Zuckersaure," 1879, Berichte Der Deutschen Chemischen Gesellschaft, 12/2:1571-1573.

Fischer, E., et al., "Ueber eine neue Pentonsaure und die zweite inactive Trioxyglutarsaure," 1891, Berichte Der Deutschen Chemischen Gesellschaft, 24/2:4216-4225.

Tiemann, F., et al., "Ueber Isozuckersaure," 1886, Berichte Der Deutschen Chemischen Gesellschaft, 19/1:1257-1281.

"Roadmap for Biomass Technologies in the United States," Dec. 2002, U.S. Dept. of Energy, 48 pages.

"Top Value Added for Chemicals from Biomass—vol. 1: Results of Screening for Potential Candidates from Sugars and Synthesis Gas," 2004, Produced by PNNL, NREL and EERE, T. Werpy and G. Petersen, Eds., U.S. Dept. of Energy, 76 pages.

"Acidum Tartaricum (U.S.P.)—Tartaric Acid," Feb. 4, 2010, Henriette's Herbal Homepage, www.henriettesherbal.com/eclectic/kings/acidum-tart.html, 5 pages.

International Search Report issued in PCT/US2010/038419, dated Jan. 31, 2011, 7 pages.

Written Opinion issued in PCT/US2010/038419, dated Jan. 31, 2011, 14 pages.

International Search Report issued in PCT/US2010/038422, dated Sep. 16, 2010, 6 pages.

Written Opinion issued in PCT/US2010/038422, dated Sep. 16, 2010, 11 pages.

International Search Report issued in PCT/US2010/038408, dated Feb. 2, 2011, 7 pages.

Written Opinion issued in PCT/US2010/038408, dated Feb. 2, 2011, 16 pages.

Casanova, O., et al., "Biomass into Chemicals: Aerobic Oxidation of 5-Hydroxymethyl-2-Furfural into 2,5-Furandicarboxylic Acid with Gold Nanoparticle Catalysts," 2009, ChemSusChem, 2:1138-1144.

Clarke, J.K.A., et al., "Preparation of Supported Platinum-Gold Catalysts and Alkane Reactions on Selected Platinum and Platinum-Gold Supported Clusters," 1984, App Catalysis, 9:85-108.

Dimitratos, N., et al., "Synergetic Effect of Platinum or Palladium on Gold Catalyst in the Selective Oxidation of D-Sorbitol," 2005, Catalysis Letters, 99:3-4:181-185.

Dirkx, J., et al., "The Preparation of D-Glucaric Acid by the Oxidation of D-Gluconic Acid Catalysed by Platinum on Carbon," 1977, Carbohydrate Research, 59:63-72.

Ibert, M., et al., "Determination of the Side-Products Formed During the Nitroxide-Mediated Bleach Oxidation of Glucose to Glucaric Acid," 2002, Carbohydrate Res, 337:1059-1063.

Lewkowski, J., "Synthesis, Chemistry and Applications of 5-Hydroxymethylfurfural and its Derivatives," 2001, Arkivoc (i):17-54.

Mallat, T., et al., "Oxidation of Alcohols with Molecular Oxygen on Solid Catalysts," 2004, Chem Rev, 104:3037-3058.

Mamman, A.S., et al. "Furfural: Hemicellulose/xylose-Derived Biochemical," 2008, Biofuels, Bioprod. Bioref., 2:438-454.

Mehltretter, C.L., et al., "Sugar Oxidation, Saccharic and Oxalic Acids by the Nitric Acid Oxidation of Dextrose," 1953, Ag and Food Chem, 1/12:779-783.

Merbouh, N., et al., "Facile Nitroxide-mediated Oxidations of D-Glucose to D-Glucaric Acid," 2001, Carbohydrate Res, 336:75-78.

Moore, J.A., et al., "An Improved Hydrogenation for the Preparation of Tetrahydrofuran cis-2,5-Dicarboxylic Acid," 1972, Organic Preparations and Procedures Int., 4/6:289-292.

(56) References Cited

OTHER PUBLICATIONS

Moreau, C., et al., "Recent Catalytic Advances in the Chemistry of Substituted Furans from Carbohydrates and in the Ensuing Polymers," 2004, Topics in Catalysis, 27/1-4:11-30.
Niu, W., et al., "Benzene-Free Synthesis of Adipic Acid," 2002, Biotechnol Prog, 18:201-211.
Ortiz-Soto, L.B., et al., "Structure-Sensitivity of Propylene Hydrogenation Over Cluster-Derived Bimetallic Pt—Au Catalysts," 2006, Catalysis Letters, 107/1-2:13-17.
Pamuk, V., et al., "The Preparation of D-Glucaric Acid by Oxidation of Molasses in Packed Beds," 2001, J Chem Technol Biotechnol, 76:186-190.
Prati, L., et al., "Effect of Gold Addition on Pt and Pd Catalysts in Liquid Phase Oxidations," 2007, Topics in Catalysis, 44/1-2:319-324.
Röper, H., "Selective Oxidation of D-Glucose: Chiral Intermediates for Industrial Utilization," 1991, Carbohydrates as Organic Raw Materials, F.W. Lichtenhaler (Ed), Verlag Chemie, Weinheim, Germany, pp. 267-288.
Shen, Y., et al., "Efficient Synthesis of Lactic Acid by Aerobic Oxidation of Glycerol on Au—Pt/TiO2 Catalysts," 2010, Chem Eur J, 16:7368-7371.
Smits, P.C.C., et al., "The Selective Oxidation of Aldoses and Aldonic Acids to 2-Ketoaldonic Acids with Lead-Modified Platinum-on-Carbon Catalysts," 1986, Carbohydrate Res, 153:227-235.
Smits, P.C.C., et al., "Lead Modified Platinum on Carbon Caralysts for the Selective Oxidation of (2–) Hydroxycarbonic Acids, and Especially Polyhydroxycarbonic Acids to Their 2-Keto Derivatives," 1987, App Catalysis, 33:83-96.
Thaburet, J-F., et al., "TEMPO-mediated Oxidation of Maltodextrins and D-Glucose: Effect of pH on the Selectivity and Sequestering Ability of the Resulting Polycarboxylates," 2001, Carbohydrate Res, 330:21-29.
Wenkin, M., et al., "Influence of Metallic Precursors on the Properties of Carbon-Supported Bismuth-Promoted Palladium Catalysts for the Selective Oxidation of Glucose to Gluconic Acid," 1996, App Catalysis A: General, 148:181-199.
Yong, G., et al., "Efficient Catalytic System for the Selective Production of 5-Hydroxymethylfurfural from Glucose and Fructose," 2008, Angew Chem Int Ed, 47:9345-9348.
Dijkgraaf, P.J.M., "Oxidation of Glucose to Glucaric Acid by Pt/C Catalysts," 1989, 105 pages, Thesis, Technische Universiteit Eindhoven.
Lichtenthaler, F.W., et al., "Carbohydrates as Green Raw Materials for the Chemical Industry," 2004 C.R. Chimie 7:65-90.
Merbouh, N., et al., "4-AcNH-TEMPO-Catalyzed Oxidation of Aldoses to Aldaric Acids Using Chlorine or Bromine as Terminal Oxidants," 2002, J Carbohydrate Chem, 21/1&2: 65-77.
International Search Report issued in PCT/US2010/060143 dated Apr. 5, 2011, 6 pages.
Written Opinion issued in PCT/US2010/060143 dated Apr. 5, 2011, 9 pages.
Scifinder Search Results on "Xylaric Acid"—search conducted on Mar. 15, 2010, 11 Pages.
Gao, S., et al., "Low-Molecular-Weight and Oligomeric Components in Secondary Organic Aerosol from the Ozonolysis of Cycloalkenes and α-Pinene," 2004, J Phys Chem A, 108:10147-10164.
Guneral, F., et al., "Age-Related Reference Values for Urinary Organic Acids in a Healthy Turkish Pediatric Population," 1994, Clin Chem, 40(6):862-868.
Pankow, J.F., et al., "Modeling the Formation of Secondary Organic Aerosol. 1. Application of Theoretical Principles to Measurements Obtained in the α-Pinene/, β-Pinene/, Sabinene/, Δ3-Carene/, and Cyclohexene/Ozone Systems," 2001, Environ Sci Technol, 35:1164-1172.
Yang, L., et al., "Photooxidation of Dicarboxylic Acids—Part II: Kinetics, Intermediates and Field Observations," 2008, Atmospheric Environment, 42:868-880.
"Adipic Acid," compounds 24,052-4 and A2,635-7 in Aldrich Handbook of Fine Chemicals and Laboratory Equipment, Nederlands Edition, 2000, p. 40, Sigma-Aldrich, USA.
International Search Report issued in PCT/US2010/060147 dated Apr. 29, 2011, 4 pages.
Written Opinion issued in PCT/US2010/060147 dated Apr. 29, 2011, 10 pages.
Habrioux, A., et al., "Activity of Platinum-Gold Alloys for Glucose Electrooxidation in Biofuel Cells," 2007, J Phys Chem B, 111:10329-10333.
Kerzenmacher, S., et al., "Energy Harvesting by Implantable Abiotically Catalyzed Glucose Fuel Cells," 2008, J Power Sources, 182:1-17.
Second Written Opinion issued in PCT/US2010/060143 dated May 30, 2012, 6 pages.
White, J.M., et al. Opportunities for Catalysis in the 21st Century, 2002, BESAC Committee Report, 47 Pages.
Database Caplus Chemical Abstracts Service, Columbus, Ohio, US; Database Accession No. 1987:477541, Abstract of Bitsi et al., Journal of Organometallic Chemistry (1986), 310(1 ), 115-19.

* cited by examiner

OXIDATION CATALYSTS

REFERENCE TO RELATED APPLICATIONS

This application is a continuation-in-part of U.S. application Ser. No. 12/814,188, filed Jun. 11, 2010, the entire content of which is incorporated herein by reference.

FIELD OF THE INVENTION

The present invention generally relates to catalysts comprised of platinum and gold. The catalysts of the present invention are useful for the selective oxidation of compositions comprised of a primary alcohol and at least one secondary alcohol to carboxylic acids or derivatives thereof. The catalysts of the present invention are particularly useful for selective oxidative chemocatalytic conversion of carbohydrates to carboxylic acids. More particularly, the catalysts of the present invention are useful for the selective oxidation of glucose to glucaric acid or derivatives thereof. The present invention is also directed to processes for the manufacture of such catalysts. The present invention is further directed to processes for converting glucose to glucaric acid and/or derivatives thereof using such catalysts.

BACKGROUND OF THE INVENTION

Crude oil is currently the source of most commodity and specialty organic chemicals. Many of these chemicals are employed in the manufacture of polymers and other materials. Examples include ethylene, propylene, styrene, bisphenol A, terephthalic acid, adipic acid, caprolactam, hexamethylene diamine, adiponitrile, caprolactone, acrylic acid, acrylonitrile, 1,6-hexanediol, 1,3-propanediol, and others. Crude oil is first refined into hydrocarbon intermediates such as ethylene, propylene, benzene, and cyclohexane. These hydrocarbon intermediates are then typically selectively oxidized using various processes to produce the desired chemical. For example, crude oil is refined into cyclohexane which is then selectively oxidized to "KA oil" which is then further oxidized for the production of adipic acid, an important industrial monomer used for the production of nylon 6,6. Many known processes are employed industrially to produce these petrochemicals from precursors found in crude oil. For example, see *Ullmann's Encyclopedia of Industrial Chemistry*, Wiley 2009 (7th edition), which is incorporated herein by reference.

For many years there has been interest in using biorenewable materials as a feedstock to replace or supplement crude oil. See, for example, Klass, *Biomass for Renewable Energy, Fuels, and Chemicals, Academic Press*, 1998, which is incorporated herein by reference. Moreover, there have been efforts to produce carboxylic acids from renewable resources using processes involving a combination of biocatalytic and chemocatalytic processes. See, for example, "Benzene-Free Synthesis of Adipic Acid", Frost et al. Biotechnol. Prog. 2002, Vol. 18, pp. 201-211, and U.S. Pat. Nos. 4,400,468, and 5,487,987.

One of the major challenges for converting biorenewable resources such as carbohydrates (e.g., glucose derived from starch, cellulose or sucrose) to current commodity and specialty chemicals is the selective conversion of the primary alcohol (hydroxyl) group to a carboxyl group (COOH) in the presence of at least a secondary alcohol group.

Glucose can be obtained from various carbohydrate-containing sources including conventional biorenewable sources such as corn grain (maize), wheat, potato, cassava and rice as well as alternative sources such as energy crops, plant biomass, agricultural wastes, forestry residues, sugar processing residues and plant-derived household wastes. More generally, biorenewable sources include any renewable organic matter that includes a source of carbohydrates such as, for example, switch grass, miscanthus, trees (hardwood and softwood), vegetation, and crop residues (e.g., bagasse and corn stover). Other sources can include, for example, waste materials (e.g., spent paper, green waste, municipal waste, etc.).

Carbohydrates such as glucose may be isolated from biorenewable materials using methods that are known in the art. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007; Furia, Starch in the Food Industry, Chapter 8, *CRC Handbook of Food Additives* $2^{nd}$ Edition CRC Press, 1973. See also chapters devoted to Starch, Sugar and Syrups within *Kirk-Othmer Encyclopedia of Chemical Technology* $5^{th}$ Edition, John Wiley and Sons 2001. Also, processes to convert starch to glucose are known in the art, see, for example, Schenck, "Glucose and Glucose-containing Syrups" in *Ullmann's Encyclopedia of Industrial Chemistry*, Wiley-VCH 2009. Furthermore, methods to convert cellulose to glucose are known in the art, see, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007.

The selective oxidation of glucose to glucaric acid has been attempted by using oxidation methods that employ platinum catalysts. See, for example, U.S. Pat. No. 2,472,168, which illustrates a method for the preparation of glucaric acid from glucose using a platinum catalyst in the presence of oxygen and a base. Further examples of the preparation of glucaric acid from glucose using a platinum catalyst in the presence of oxygen and a base are illustrated in the *Journal of Catalysis* Vol. 67, p. 1-13, and p. 14-20 (1981). Other oxidation methods have also been employed; see, for example, U.S. Pat. Nos. 6,049,004, 5,599,977, and 6,498,269, WO 2008/021054 and *J. Chem. Technol. Biotechnol.* Vol. 76, p. 186-190 (2001); *J. Agr. Food Chem.* Vol. 1, p. 779-783 (1953); *J. Carbohydrate Chem.* Vol. 21, p. 65-77 (2002); *Carbohydrate Res.* Vol. 337, p. 1059-1063 (2002); *Carbohydrate Res.* 336, p. 75-78 (2001); and *Carbohydrate Res.* Vol. 330, p. 21-29 (2001). However, these processes suffer from economic shortcomings resulting from, among other matters, process yield limitations, low conversion rates, and limited selectivity due to shortcomings in the performance of existing catalysts. None of these catalysts or the processes employing them are used industrially for the selective oxidation of glucose-containing carbohydrates to manufacture specialty or industrial carboxylic acids or derivatives thereof.

Thus, there remains a need for new, industrially scalable catalysts for the selective and commercially-meaningful conversion of a primary hydroxyl group to a carboxyl group of compositions comprising a primary hydroxyl group and at least a secondary hydroxyl group. Desirably, there is the need to convert biorenewable materials such as, for example, carbohydrates or polyols, to specialty or industrial carboxylic acids and derivatives thereof, and more particularly, e.g., to convert glucose (derived from starch, cellulose or sucrose) to important chemicals such as glucaric acid and derivatives thereof.

SUMMARY OF THE INVENTION

The present invention is directed generally to catalyst compositions comprising gold and discrete particles of platinum on a support wherein the ratio of platinum to gold on the support is in the range of from about 100:1 to about 1:4 and the platinum is substantially present on the support as Pt(0).

The present invention is also directed to catalyst compositions useful for the selective conversion of a primary hydroxyl group of compositions comprising a primary hydroxyl group and at least a secondary hydroxyl group to a carboxyl group wherein the catalyst compositions comprise platinum and gold.

The present invention is further directed to catalyst compositions comprising gold and discrete particles of platinum on a support wherein (a) the ratio of platinum to gold on the support is in the range of from about 100:1 to about 1:4, (b) the platinum is substantially present on the support as Pt(0), and (c) the particle sizes of the platinum particles are substantially in the range of from about 2 to about 50 nanometers.

Moreover, the present invention is directed to catalyst compositions comprising particles comprising gold and particles of platinum on a support wherein (a) the ratio of platinum to gold on the support is in the range of from about 100:1 to about 1:4, (b) the platinum is substantially present on the support as Pt(0), (c) the particle sizes of the platinum particles are substantially in the range of from about 2 to about 50 nanometers, and (d) the particle sizes of the gold-containing particles are substantially in the range of about 2 to about 20 nanometers.

Further, the present invention is directed to catalyst compositions produced by processes comprising the steps of a) providing a solid support, b) contacting the support with at least one gold-containing compound, c) contacting the support and the at least one gold-containing compound with a base, d) contacting the support with at least one platinum-containing compound, and e) treating the support and the at least one platinum-containing compound under conditions sufficient to create on the support particles comprising gold and particles comprising platinum, wherein the ratio of platinum to gold on the support is in the range of from about 100:1 to about 1:4, the platinum is substantially present on the support as Pt(0), and the particle sizes of the platinum particles are substantially in the range of from about 2 to about 50 nanometers.

The present invention is further directed to processes for preparing glucaric acid or derivatives thereof comprising reacting glucose with a source of oxygen in the presence of a catalyst comprising gold and platinum and in the substantial absence of added base.

Other objects and features will become apparent and/or will be pointed out hereinafter.

DESCRIPTION OF THE PREFERRED EMBODIMENTS

Figure 1:
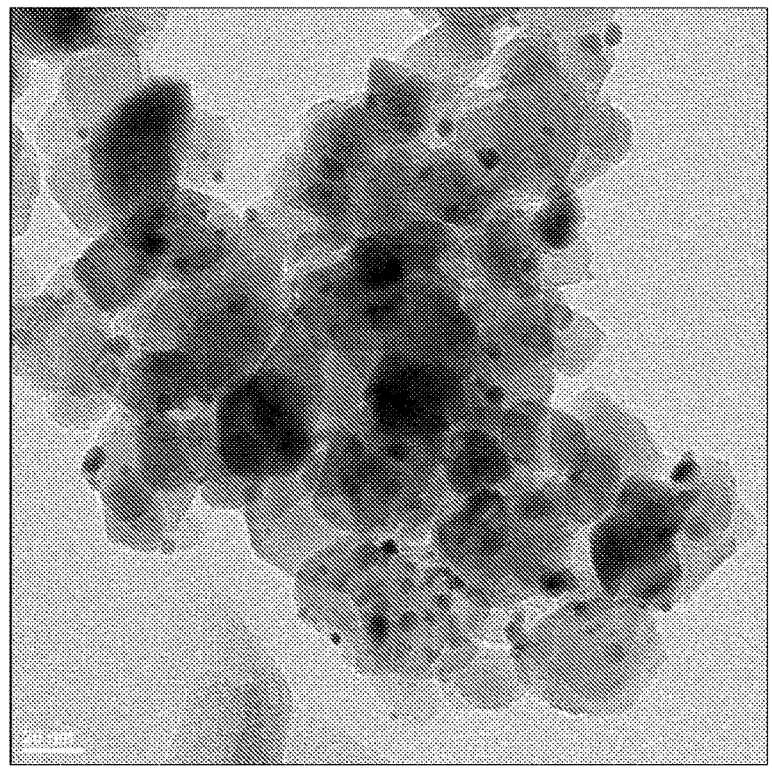
FIG. 1 is a TEM photograph of fresh catalyst prepared in accordance with Example 2 (entry 21) comprised of 4 wt % platinum and 4 wt % gold on Saint Gobain Norpro Titania ST31119 particles of 150-250 µm at magnification of 88 k.

In accordance with the present invention, applicants disclose catalyst compositions comprised of platinum and gold.

The catalyst compositions of the present invention are particularly useful in the selective oxidation of a primary alcohol to a carboxyl in compositions comprising the primary hydroxyl (alcohol) group and at least a secondary hydroxyl (alcohol) group. High conversion and selectivity, coupled with unexpectedly high yield, results from the use of the catalysts of the present invention. Conversion of carbohydrates and, more particularly, glucose and derivatives thereof to oxidation products such as glucaric acid and derivatives thereof is especially efficacious employing the catalysts of the present invention.

The catalyst compositions of the present invention comprise platinum and gold. These catalysts are heterogeneous, solid-phase catalysts. In various embodiments, the metals are present at a surface of a support (i.e., at one or more surfaces, external or internal). Suitable catalyst supports include carbon, surface treated aluminas (such as passivated aluminas or coated aluminas), silicas, titanias, zirconias, zeolites, montmorillonites, and modifications, mixtures or combinations thereof. Preferred support materials include titanias, zirconias, silicas and montmorillonites. Preferred support materials may be modified using methods known in the art such as heat treatment, acid treatment, steam treatment or by the introduction of a dopant (e.g., metal-doped titanias or metal-doped zirconias such as tungstated-zirconia). The catalyst support may be treated so as to promote the preferential deposition of the metals on the outer surface of the support so as to create a shell type catalyst. The supports may be in a variety of form such as powders, pellets, spheres, extrudates and xerogels.

Catalyst performance in general is in significant part dependent upon the degree of uniformity of dispersion of the metals on the support. The platinum and gold-containing catalysts of the present invention may be produced by deposition procedures known in the art including, but not limited to, incipient wetness, ion-exchange and deposition-precipitation. In various embodiments, a uniform dispersion can be effected by forming a heterogeneous slurry of the support in combination with solubilized metal complexes. In certain embodiments, the supports may be initially dispersed in a liquid such as water. Thereafter, in such embodiments, the solubilized metal complexes may be added to the slurry containing the support. The heterogeneous mixture of solid and liquids can then be stirred, mixed and/or shaken to enhance the uniformity of dispersion of the catalyst, which, in turn, enables the more uniform deposition of metals on the surface of the support upon removal of the liquids and additional treatments as may be needed and more fully described hereinafter.

The gold component of the catalysts of the present invention is typically added to the support as a solubilized constituent to enable the formation of a uniform suspension.

A base is then added to the suspension in order to create an insoluble gold complex which can be more uniformly deposited onto the support. For example, in various embodiments, the solubilized gold constituent is provided to the slurry as, for example, $HAuCl_4$. Upon creation of a well dispersed, heterogeneous mixture, a base is added to the slurry to form an insoluble gold complex which then deposits on the surface of the support. Although any base which can effect the formation of an insoluble gold complex is useable, in various embodiments nitrogen-containing bases such as ammonia or urea are employed. It may be desirable, though not required, to collect the support on which has been deposited the insoluble gold complex prior to adding the platinum-containing constituent, which collection can readily be accomplished by any of a variety of means known in the art such as, for example, centrifugation. The collected solids may optionally be washed and then may be heated to dry. Heating may also be employed so as to reduce the gold complex on the support to Au(0). Heating may be conducted at temperatures ranging from about 60° C. (to dry) up to about 500° C. (at which temperature the gold can be effectively reduced). In various embodiments, the heating step may be conducted in the presence of a reducing or oxidizing atmosphere in order to promote the reduction of the complex to deposit the gold onto the support as Au(0). Heating times vary depending upon, for example, the objective of the heating step and the decomposition rate of the base added to form the insoluble complex, and the heating times can range from a few minutes to a few days. More typically, the heating time for the purpose of drying ranges from about 2 to about 24 hours and for reducing the gold complex is on the order of about 1-4 hours.

In various embodiments, the concentration of the support in the slurry can be in the range of about 1 to about 100 g of solid/liter of slurry, and in other embodiments the concentration can be in the range of about 5 to about 25 g of solid/liter of slurry.

Mixing of the slurry containing the soluble gold-containing compound is continued for a time sufficient to form at least a reasonably uniform suspension. Appropriate times can range from minutes to a few hours. After addition of the base to convert the gold-containing compound to an insoluble gold-containing complex, the uniformity of the slurry should be maintained for a time sufficient to enable the insoluble complex to be formed and deposit on the support. In various embodiments, the time can range from a few minutes to several hours.

The gold deposited on surfaces of the support forms particles comprising gold. More typically, the gold on the fresh catalyst exists as particles of Au(0) and/or as gold-containing alloys such as gold-platinum alloys. The particles size will vary, but the particles are substantially of a size generally less than or equal to about 20 nanometers (nm). By "size" we mean the largest, straight line dimension of the particle, and by "substantially" we mean at least about 50%. More typically, the particles are substantially of a size in the range of about 2 to about 15 nm and, more preferably, in the range of about 5 to about 12 nm.

Platinum is typically added to the support or support-containing slurry after deposition of gold onto the support and, more preferably, after decomposition of the base. Alternatively, the platinum may be added to the support or support-containing slurry prior to the addition of the solubilized gold compound provided the platinum present on the support is in a form that will not be re-dissolved upon the addition of base used to promote the deposition of gold onto the support. The platinum is typically added as a solution of a soluble precursor or as a colloid. Platinum may be added as a compound selected form the group of platinum (II) nitrate, platinum (II) acetylacetonate (acac), tetraamineplatinum (II) nitrate, tetraamineplatinum (II) hydrogenphosphate and tetraamineplatinum (II) hydroxide. More preferred compounds include platinum(II) nitrate, platinum(II) acetylacetonate (acac), and tetraamine platinum(II) nitrate.

Subsequent to the addition of the platinum compound, the support slurry and platinum-containing compound is dried. Drying may be conducted at room temperature or at a temperature up to about 120° C. More preferably, drying is conducted at a temperature in the range of about 40° C. to about 80° C. and more preferably still at about 60° C. The drying step may be conducted for a period of time ranging from about a few minutes to a few hours. Typically, the drying time is in the range of about 6 hours to about 24 hours.

After drying the support having the platinum compound deposited thereon, it is subjected to at least one thermal treatment in order to reduce platinum deposited as Pt(II) or Pt(IV) to Pt(0). The thermal treatment(s) can be conducted in any reducing atmosphere. In various embodiments the thermal treatment(s) is (are) conducted under a forming gas atmosphere. Alternatively, a liquid reducing agent may be employed to reduce the platinum; for example, hydrazine or formaldehyde may be employed to effect the requisite reduction of the platinum. The atmosphere under which the thermal treatment is conducted is dependent upon the platinum compound employed, with the objective being substantially converting the platinum on the support to Pt(0).

The temperatures at which the thermal treatment(s) is (are) conducted generally range from about 200° C. to about 600° C. More typically, the temperatures of the thermal treatment(s) range from about 200° C. to about 500° C. and, preferably, the range is from about 200° C. to bout 400° C. The thermal treatment is typically conducted for a period of time ranging from about 1 hour to about 5 hours. More typically, the treatment is conducted for a period of time ranging from about 1 hour to about 3 hours. For example, at a thermal treatment temperature of about 350° C., the time of the treatment is about 3 hours.

The platinum deposited on surfaces of the support forms particles. Generally, the platinum on the fresh catalyst exists substantially as particles of essentially Pt(0) and/or as platinum-containing alloys such as gold-platinum alloys. In various embodiments, the catalysts will comprise discrete particles of platinum, particles comprising platinum and gold, and, possibly, particles of gold. In certain preferred embodiments, essentially all of the particles consisting essentially of platinum exist as Pt(0). The particles size will vary, but the particles are substantially of a size generally less than or equal to about 50 nanometers (nm). By "size" we mean the largest, straight line dimension of the particle. By "substantially" we mean at least about 50%. More typically, the particles are substantially of a size in the range of about 2 to about 50 nm and, preferably, in the range of about 5 to about 30 nm. More preferably, the particles are at least substantially in the range of about 5 to about 20 nm and, more preferably, in the range of about 8 to about 12 nm.

The platinum:gold molar ratio may vary, for example, from about 100:1 to about 1:4, from about 50:1 to about 1:4, from about 10:1 to about 1:4, or more preferably from about 3:1 to about 1:4. More preferably still, the platinum:gold molar ratio may vary, for example, from about 3:1 to about 1:2. Even more preferably, the molar ratio of platinum:gold is in the range of about 2:1 to about 1:1.

Figure 2:
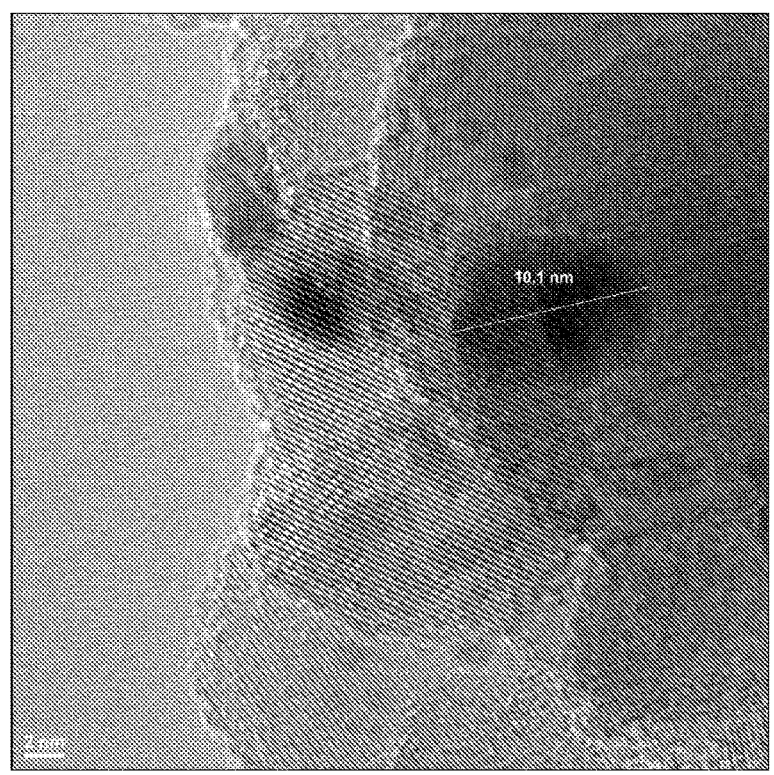
FIG. 2 is a TEM photograph of fresh catalyst of the present invention as described with respect to FIG. 1 at magnification of 530 k.
Figure 3:
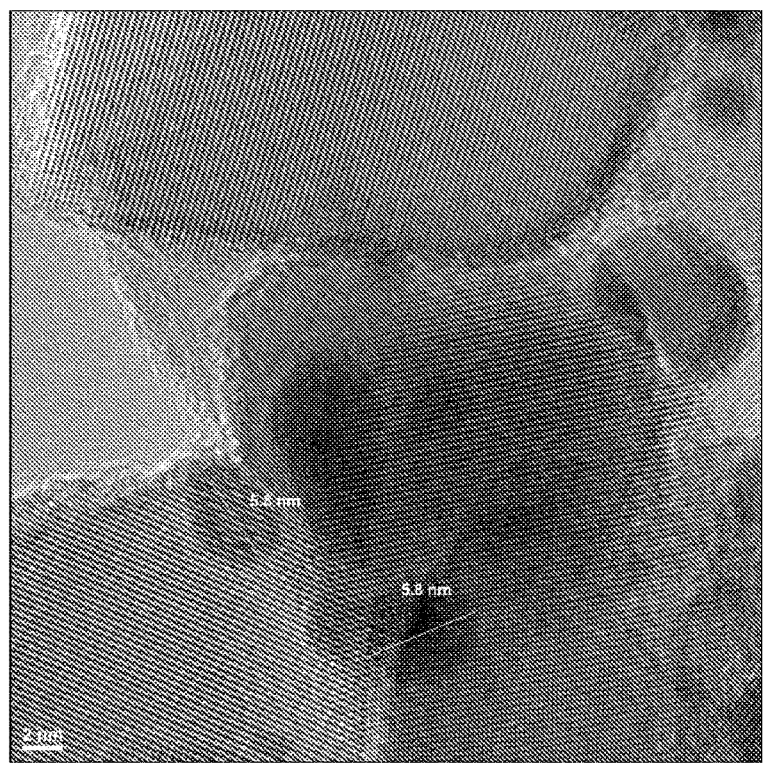
FIG. 3 is a TEM photograph of fresh catalyst of the present invention as described with respect to FIG. 1 at magnification of 530 k.
Figure 4:
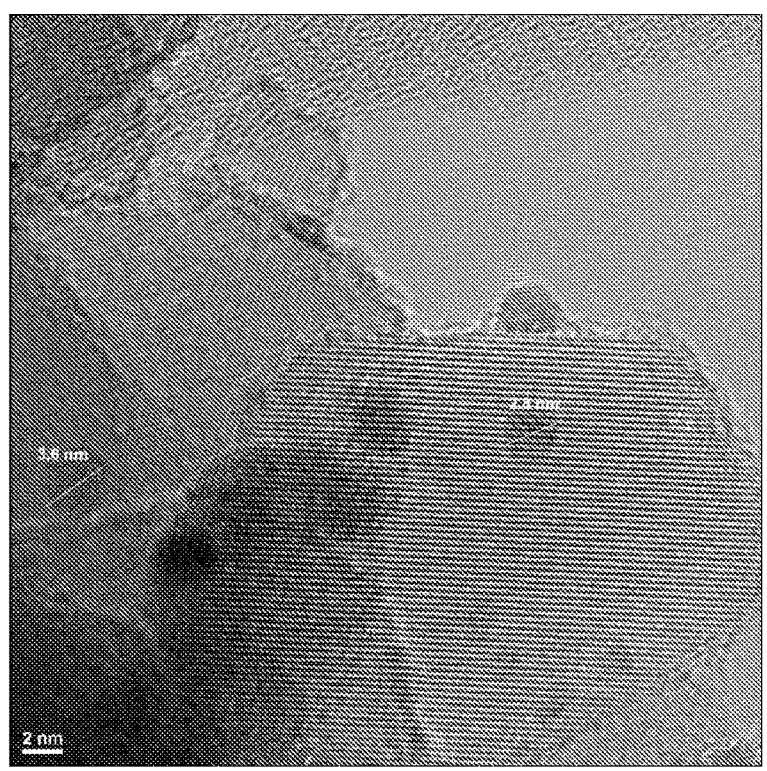
FIG. 4 is a TEM photograph of fresh catalyst of the present invention as described with respect to FIG. 1 at magnification of 530 k.

FIG. 1 shows a TEM photograph taken at 88 k magnification of a 4 wt % Au-4 wt % Pt catalyst of the present invention prepared in accordance with Example 2 (entry 21). As shown, metal particles (dark) on the support (light) are less than about 50 nm, at least about 50% are less than about 20 nm, and at least about 50% are less than about 15 nm, but generally are equal to or greater than about 2 nm. FIGS. 2, 3 and 4 are photographs of the same fresh catalyst taken at magnifications of 530 k showing clearly the presence of metallic particles of about 10 nm and 6 nm, and as small as about 2 nm.

In various other embodiments, a third metal (M3) may be added to produce a Pt/Au/M3 catalyst wherein the M3 metal is not platinum or gold. In yet other embodiments a fourth metal (M4) may be added to produce a Pt/Au/M3/M4 catalyst wherein the M4 metal is not platinum or gold and also not the same metal as the M3 metal. The M3 metal and M4 metal may each be selected from group 6 or group 10 metals, with palladium being a more preferred group 10 metal and tungsten being a more preferred group 6 metal.

The total metal loading on the final catalyst (i.e., excluding any metal that is from the support) is generally less than or equal to about 10 wt % relative to the total catalyst weight. Generally, the total metal loading is in the range of from about 1% to about 10%. More typically, the total weight percent ranges from about 1% to about 8%, and more preferably from about 1% to about 4%.

Glucose is effectively converted to glucaric acid in high yield by reacting glucose with oxygen (as used herein, oxygen can be supplied to the reaction as air, oxygen-enriched air, oxygen alone, or oxygen with other constituents substantially inert to the reaction) in the presence of the catalyst compositions of the present invention and in the absence of added base according to the following reaction:

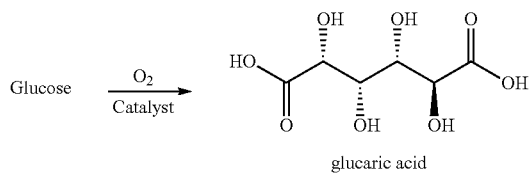 [SMILES: "O2" ; O=C(O)[C@@H](O)[C@@H](O)[C@H](O)[C@@H](O)C(=O)O]

Conducting the oxidation reaction in the absence of added base and in the presence of the catalyst compositions of the present invention does not lead to significant catalyst poisoning effects and oxidation catalyst selectivity is maintained. In fact, catalytic selectivity can be maintained to attain glucaric acid yield in excess of 60%, even 65% and, in some embodiments, attain yields in excess of 70% or higher. The absence of added base advantageously facilitates separation and isolation of the glucaric acid, thereby providing a process that is more amenable to industrial application, and improves overall process economics by eliminating a reaction constituent. The "absence of added base" as used herein means that base, if present (for example, as a constituent of a feedstock), is present in a concentration which has essentially no effect on the efficacy of the reaction (i.e., the oxidation reaction is being conducted essentially free of added base). It has also been discovered that this oxidation reaction can also be conducted in the presence of a weak carboxylic acid, such as acetic acid, in which glucose is soluble. The term "weak carboxylic acid" as used herein means any unsubstituted or substituted carboxylic acid having a pKa of at least about 3.5, more preferably at least about 4.5 and, more particularly, is selected from among unsubstituted acids such as acetic acid, propionic acid or butyric acid, or mixtures thereof.

The initial pH of the reaction mixture is no greater than about 7, and is typically less than 7 such as, for example, 6 or less (e.g., when a weak carboxylic acid is used to solubilize at least a portion of the glucose). The initial pH of the reaction mixture is the pH of the reaction mixture prior to contact with oxygen in the presence of an oxidation catalyst. It is expected that the pH of the reaction mixture after oxygen contact will vary as the reaction proceeds. It is believed that as the concentration of the glucaric acid increases (as the reaction proceeds) the pH will decrease from the initial pH.

The process of producing glucaric acid or derivatives thereof from carbohydrate such as glucose can be conducted with the catalysts of the present invention in the essential absence of nitrogen as an active reaction constituent. Typically, nitrogen is employed in known processes as an oxidant such as in the form of nitrate, in many instances as nitric acid. The use of nitrogen in a form in which it is an active reaction constituent, such as nitrate or nitric acid, results in the need for $NO_x$ abatement technology and acid regeneration technology, both of which add significant cost to the production of glucaric acid from these known processes, as well as providing a corrosive environment which may deleteriously affect the equipment used to carry out the process. By contrast, for example, in the event air or oxygen-enriched air is used in the oxidation reaction of the present invention as the source of oxygen, the nitrogen is essentially an inactive or inert constituent. Thus, for example, an oxidation reaction employing air or oxygen-enriched air is a reaction conducted essentially free of nitrogen in a form in which it would be an active reaction constituent.

Generally, the temperature of the oxidation reaction mixture is at least about 40° C., more typically 60° C., or higher. In various embodiments, the temperature of the oxidation reaction mixture is from about 40° C. to about 150° C., from about 60° C. to about 150° C., from about 70° C. to about 150° C., from about 70° C. to about 140° C., or from about 80° C. to about 140° C.

Typically, the partial pressure of oxygen is at least about 15 pounds per square inch absolute (psia) (104 kPa), at least about 25 psia (172 kPa), at least about 40 psia (276 kPa), or at least about 60 psia (414 kPa). In various embodiments, the partial pressure of oxygen is up to about 1000 psia (6895 kPa), or more typically in the range of from about 15 psia (104 kPa) to about 500 psia (3447 kPa).

The oxidation reaction is typically conducted in the presence of a solvent to glucose. Solvents suitable for the oxidation reaction include water and weak carboxylic acids such as acetic acid. Utilization of weak carboxylic acid as a solvent adds cost to the process which cost, as a practical matter, must be balanced against any benefits derived from the use thereof. Thus, suitable solvents for the present invention include water, mixtures of water and weak carboxylic acid, or weak carboxylic acid. The catalyst compositions of the present invention remain stable in the presence of the solvent.

In general, the oxidation reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that glucose, oxygen, any solvent, and the oxidation catalyst may be introduced into a suitable reactor separately or in various combinations.

The reaction product of the oxidation step will, as described above, contain glucaric acid in considerable and heretofore unexpected fraction, but may also contain derivatives thereof, such as glucarolactones. These glucarolactones, like glucaric acid, constitute a hydrodeoxygenation substrate which is particularly amenable to the production of adipic acid product as hereinafter described. Glucarolactones which may be present in the reaction mixture resulting from the oxidation step include mono and di-lactones such as D-glucaro-1,4-lactone, D-glucaro-6,3-lactone, and D-glucaro-1,4:6,3-dilactone. One advantage of higher concentrations of glucarolactones is further improvement in the economics of a downstream hydrodeoxygenation step for producing adipic acid resulting from a reduction in the amount of water produced.

Glucaric acid produced in accordance with the above may be converted to various other glucaric acid derivatives, such as salts, esters, ketones, and lactones. Methods to convert carboxylic acids to such derivatives are known in the art, see, for example, Wade, *Organic Chemistry* $3^{rd}$ ed, Prentice Hall 1995.

Adipic acid is an example of an industrially significant product that can be prepared by chemocatalytic conversion of a glucose source via intermediates such as glucaric acid or derivatives thereof, which intermediates are attainable from the use of the catalysts compositions of the present invention. In this process, a hydrodeoxygenation substrate comprising glucaric acid or derivatives thereof is convertible to an adipic acid product.

The hydrodeoxygenation substrate comprises a compound of the Formula I:

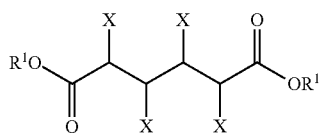

wherein X is independently hydroxyl, oxo, halo, acyloxy or hydrogen provided that at least one X is not hydrogen; $R^1$ is independently a salt-forming ion, hydrogen, hydrocarbyl, or substituted hydrocarbyl; or a mono- or di-lactone thereof.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

Salt forming ions include, without limitation, for example ammonium ions and metal ions (e.g., alkali and alkaline earth metals). When $R^1$ is a salt forming ion (i.e., a cation), the carboxyl group may be considered to be anion (i.e., carboxylate anion).

In various embodiments, the hydrodeoxygenation substrate comprises a compound of Formula I, wherein X is hydroxyl and $R^1$ is independently a salt-forming ion, hydrogen, hydrocarbyl, or substituted hydrocarbyl.

As shown in Formula I, the hydrodeoxygenation substrate contains a six carbon chain comprising four chiral centers. As a result several stereoisomers are possible.

The hydrodeoxygenation substrate may also contain various ketones. For example, not wishing to be bound by theory, when glucaric acid is further oxidized, ketones such as 2-keto-glucaric acid (2,3,4-trihydroxy-5-oxohexanedioic acid) and 3-keto-glucaric acid (2,3,5-trihydroxy-4-oxohexanedioic acid) may be formed.

The hydrodeoxygenation substrate may comprise various lactones derived from glucaric acid. For example, not wishing to be bound by theory, it is believed that various mono- and di-lactones are present in equilibrium with glucaric acid in aqueous solution, including for example, D-glucaro-1,4-lactone, D-glucaro-6,3-lactone, and D-glucaro-1,4:6,3-dilactone. Moreover, processes have been developed to quantitatively convert glucaric acid or a salt thereof in solution to one or more lactones and recover a substantially pure lactone stream. For example see "Convenient Large-Scale Synthesis of D-Glucaro-1,4:6,3-dilactone" Gehret et al., J. Org. Chem., 74 (21), pp. 8373-8376 (2009). Also, lactones such as L-threo-4-deoxy-hex-4-enaro-6,3-lactone and L-erythro-4-deoxy-hex-4-enaro-6,3-lactone may form from the thermal decomposition of D-Glucaro-1,4:6,3-dilactone.

Therefore, in various embodiments, the hydrodeoxygenation substrate comprises D-glucaro-1,4-lactone. In these and other embodiments, the hydrodeoxygenation substrate comprises D-glucaro-6,3-lactone. Still further, in these and other embodiments, the hydrodeoxygenation substrate comprises D-glucaro-1,4:6,3-dilactone. In these and other embodiments, the hydrodeoxygenation substrate comprises L-threo-4-deoxy-hex-4-enaro-6,3-lactone. Still even further, in these and other embodiments, the hydrodeoxygenation substrate comprises L-erythro-4-deoxy-hex-4-enaro-6,3-lactone.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.
Catalyst Testing Protocol 1
Catalyst (approx. 8 mg) was weighed into a glass vial insert followed by addition of an aqueous glucose solution (250 μl of 10 wt %). The glass vial insert was loaded into a reactor and the reactor was closed. The atmosphere in the reactor was replaced with oxygen and pressurized to 75 psig at room temperature. Reactor was heated to 90° C. and maintained at 90° C. for 5 hours while vials were shaken. After 5 hours, shaking was stopped and reactor was cooled to 40° C. Pressure in the reactor was then slowly released. The glass vial insert was removed from the reactor and centrifuged. The clear solution was diluted with deionized water and analyzed by ion-chromatography (IC) with conductivity and Corona CAD detection (IC-conductivity-CAD). Samples for IC analysis were prepared by adding to the reaction vial 750 µL water followed by 25-fold dilution. Product yields were determined using a Dionex ICS-3000 Chromatography system equipped with Corona CAD detector (ESA Biosciences) The products were first separated on an Ionpac® AS11-HC column and then quantified by conductivity and Corona CAD detection through comparison with calibration standards.

Catalyst Testing Protocol 2

Catalyst (approx. 75 mg) was weighed into a glass vial insert followed by addition of an aqueous glucose solution (2.3 ml of 10 wt %). The glass vial insert was loaded into a reactor and the reactor was closed with a disposable stir paddle fitted to the reaction vessel. The atmosphere in the reactor was replaced with oxygen and pressurized to 50 psig at room temperature. The reactor was heated to a pre-set temperature in the range of 90 to 133° C. After the temperature stabilized, pressure in the reactor was increased to 400 psig by using high pressure oxygen. Stirring was turned on at 1100 rpm. Pressure of 400 psig and the pre-set temperature in the reactor were maintained for an extended period of time using computer control. When a designated reaction time was reached, oxygen feed was stopped, stirring was discontinued and the reactor was cooled to 40° C. Pressure in the reactor was then slowly released. The glass vial insert was removed from the reactor and centrifuged. The clear solution was diluted with deionized water and analyzed by IC-conductivity-CAD as described above.

Example 1

Approximately 88 µl of an aqueous solution of $HAuCl_4$ (containing 0.2254 wt % gold) was added to a suspension of 10 mg Titania P25 (Acros Organics) in deionized water (450 µl) while shaking. The suspension was shaken at room temperature for 30 min. 250 µl of an aqueous solution of $NH_4OH$ (4.0 M) was added to the above-mentioned suspension and the resulting suspension was shaken at room temperature for 2 hours. The resulting suspension was then centrifuged and supernatant was decanted. After residual liquid was removed using filter paper, the light yellow solid was dried in a 60° C. oven overnight under a dry air purge.

2.1 µl of an aqueous solution of $Pt(NO_3)_2$ (containing 7.7 wt % platinum) was added to the above solid and the mixture was agitated to impregnate the gold-containing support. The sample was dried in a 60° C. oven overnight under a dry air purge. The sample was then reduced at 350° C. under forming gas (5% $H_2$ and 95% $N_2$) atmosphere for 3 hours with 2° C./min temperature ramp rate. The final catalyst contained about 2.0 wt % gold and 2.0 wt % platinum.

By adjusting the volume and concentration of solutions of $HAuCl_4$, $NH_4OH$, and $Pt(NO_3)_2$, a series of other catalysts with various loadings of gold (0 to 8 wt %) and platinum (0 to 8 wt %) were prepared. Similar methods were also used to prepare catalysts based on other supports, including Titania ST 31119 (Saint-Gobain Norpro), Zirconia Z-1628 (Daiichi Kigenso Kagaku Kogyo), Zirconia Z-1044 (Daiichi Kigenso Kagaku Kogyo), Silica-Titania Cariact (Fuji Silysia), Silica Cariact Q-10 (Fuji Silysia), Davisil 635 (Sigma-Aldrich), and Zeolite CP 811C-300 (Zeolyst). These catalysts were tested for glucose oxidation using Catalyst testing protocol 1 and results are summarized in Table 1.

Entries 4-6, 9, 12 13, 22, 23, 28, 29, 37 38, 39, 45, 49-51, 61, 62, 67, 68, 79 and 80 are comparative entries of compositions outside the scope of the present invention. Except for Entry 51, these entries illustrate, when compared to the other entries reported in Table 1, the conversion and other benefits attainable from compositions of the present invention. Entry 51, although exhibiting a higher conversion, causes the production of non-desirable products of over-oxidation at a given glucaric acid yield which render it impractical for commercial use when compared to the catalysts of the present invention. Moreover, many industrial processes employ recycling of unreacted substrate in order to improve overall conversion and a high concentration of non-desirable products reduces the yields ultimately attainable from the feedstock.

TABLE 1

Conditions and results of glucose oxidation on gold/platinum catalysts of Example 1

| Entry | Catalyst wt. (mg) | Support | Au wt. % | Pt wt. % | Glucose Conversion (%) | Glucaric Acid Yield (%) |
|---|---|---|---|---|---|---|
| 1 | 8.3 | Silica Cariact Q-10 | 0.8 | 7.2 | 98 | 51 |
| 2 | 8.0 | Silica Cariact Q-10 | 2.8 | 1.2 | 100 | 36 |
| 3 | 8.1 | Silica Cariact Q-10 | 3.2 | 0.8 | 100 | 28 |
| 4 | 7.7 | Silica Cariact Q-10 | 4.0 | 0.0 | 99 | 4 |
| 5 | 8.4 | Silica Cariact Q-10 | 8.0 | 0.0 | 100 | 6 |
| 6 | 8.3 | Silica Davisil 635 | 0.0 | 8.0 | 96 | 44 |
| 7 | 8.2 | Silica Davisil 635 | 1.6 | 6.4 | 100 | 53 |
| 8 | 8.4 | Silica Davisil 635 | 2.4 | 1.6 | 100 | 46 |
| 9 | 8.5 | Silica Davisil 635 | 8.0 | 0.0 | 100 | 6 |
| 10 | 8.5 | Silica-Titania Cariact | 2.8 | 1.2 | 100 | 29 |
| 11 | 8.5 | Silica-Titania Cariact | 5.6 | 2.4 | 100 | 40 |
| 12 | 8.5 | Silica-Titania Cariact | 7.2 | 0.8 | 100 | 20 |
| 13 | 8.2 | Titania P25 | 0.0 | 8.0 | 86 | 33 |
| 14 | 8.4 | Titania P25 | 0.4 | 3.6 | 97 | 33 |
| 15 | 8.2 | Titania P25 | 1.2 | 2.8 | 100 | 39 |
| 16 | 7.8 | Titania P25 | 1.6 | 2.4 | 100 | 45 |
| 17 | 8.4 | Titania P25 | 1.6 | 6.4 | 100 | 62 |
| 18 | 8.3 | Titania P25 | 2.0 | 2.0 | 100 | 33 |
| 19 | 8.5 | Titania P25 | 2.4 | 5.6 | 100 | 64 |

TABLE 1-continued

Conditions and results of glucose oxidation on gold/platinum catalysts of Example 1

| Entry | Catalyst wt. (mg) | Support | Au wt. % | Pt wt. % | Glucose Conversion (%) | Glucaric Acid Yield (%) |
|---|---|---|---|---|---|---|
| 20 | 8.3 | Titania P25 | 3.2 | 0.8 | 100 | 11 |
| 21 | 7.7 | Titania P25 | 3.2 | 4.8 | 100 | 57 |
| 22 | 8.3 | Titania P25 | 3.6 | 0.4 | 100 | 5 |
| 23 | 8.0 | Titania P25 | 4.0 | 0.0 | 100 | 1 |
| 24 | 7.8 | Titania P25 | 4.0 | 4.0 | 100 | 46 |
| 25 | 7.8 | Titania P25 | 4.8 | 3.2 | 100 | 21 |
| 26 | 8.0 | Titania P25 | 5.6 | 2.4 | 100 | 18 |
| 27 | 8.2 | Titania P25 | 6.4 | 1.6 | 100 | 14 |
| 28 | 7.6 | Titania P25 | 7.2 | 0.8 | 100 | 8 |
| 29 | 7.8 | Titania P25 | 8.0 | 0.0 | 100 | 1 |
| 30 | 8.1 | Titania ST 31119 | 0.8 | 3.2 | 100 | 40 |
| 31 | 8.5 | Titania ST 31119 | 1.2 | 2.8 | 100 | 49 |
| 32 | 7.7 | Titania ST 31119 | 1.6 | 2.4 | 100 | 42 |
| 33 | 7.9 | Titania ST 31119 | 2.0 | 2.0 | 100 | 43 |
| 34 | 8.0 | Titania ST 31119 | 2.4 | 1.6 | 100 | 25 |
| 35 | 7.6 | Titania ST 31119 | 2.8 | 1.2 | 100 | 22 |
| 36 | 8.5 | Titania ST 31119 | 3.2 | 0.8 | 100 | 21 |
| 37 | 7.9 | Titania ST 31119 | 3.6 | 0.4 | 100 | 13 |
| 38 | 8.1 | Titania ST 31119 | 4.0 | 0.0 | 100 | 2 |
| 39 | 8.4 | Titania ST 31119 | 8.0 | 0.0 | 96 | 1 |
| 40 | 8.0 | Zeolite CP 811C-300 | 0.8 | 3.2 | 93 | 22 |
| 41 | 8.1 | Zeolite CP 811C-300 | 1.2 | 2.8 | 100 | 29 |
| 42 | 8.2 | Zeolite CP 811C-300 | 2.4 | 1.6 | 100 | 28 |
| 43 | 7.9 | Zeolite CP 811C-300 | 2.8 | 1.2 | 100 | 20 |
| 44 | 7.7 | Zeolite CP 811C-300 | 3.2 | 0.8 | 100 | 14 |
| 45 | 8.3 | Zeolite CP 811C-300 | 3.6 | 0.4 | 99 | 6 |
| 46 | 8.0 | Zeolite CP 811C-300 | 4.8 | 3.2 | 100 | 41 |
| 47 | 8.4 | Zeolite CP 811C-300 | 5.6 | 2.4 | 100 | 31 |
| 48 | 7.7 | Zeolite CP 811C-300 | 6.4 | 1.6 | 100 | 20 |
| 49 | 7.9 | Zeolite CP 811C-300 | 8.0 | 0.0 | 100 | 7 |
| 50 | 7.9 | Zirconia 1628 | 0.0 | 4.0 | 84 | 23 |
| 51 | 8.2 | Zirconia 1628 | 0.0 | 8.0 | 98 | 50 |
| 52 | 8.1 | Zirconia 1628 | 0.4 | 3.6 | 85 | 22 |
| 53 | 8.3 | Zirconia 1628 | 0.8 | 3.2 | 97 | 22 |
| 54 | 8.3 | Zirconia 1628 | 0.8 | 7.2 | 98 | 45 |
| 55 | 8.0 | Zirconia 1628 | 1.2 | 2.8 | 100 | 25 |
| 56 | 7.8 | Zirconia 1628 | 1.6 | 2.4 | 100 | 22 |
| 57 | 8.2 | Zirconia 1628 | 2.4 | 1.6 | 100 | 16 |
| 58 | 7.9 | Zirconia 1628 | 2.8 | 1.2 | 100 | 17 |
| 59 | 8.4 | Zirconia 1628 | 3.2 | 0.8 | 100 | 14 |
| 60 | 8.5 | Zirconia 1628 | 3.2 | 4.8 | 100 | 40 |
| 61 | 7.8 | Zirconia 1628 | 3.6 | 0.4 | 100 | 7 |
| 62 | 7.8 | Zirconia 1628 | 4.0 | 0.0 | 99 | 0 |
| 63 | 7.9 | Zirconia 1628 | 4.0 | 4.0 | 100 | 33 |
| 64 | 8.3 | Zirconia 1628 | 4.8 | 3.2 | 100 | 24 |
| 65 | 8.0 | Zirconia 1628 | 5.6 | 2.4 | 100 | 16 |
| 66 | 8.0 | Zirconia 1628 | 6.4 | 1.6 | 100 | 9 |
| 67 | 8.2 | Zirconia 1628 | 8.0 | 0.0 | 71 | 0 |
| 68 | 7.6 | Zirconia Z-1044 | 0.0 | 4.0 | 72 | 19 |
| 69 | 7.9 | Zirconia Z-1044 | 0.4 | 3.6 | 88 | 29 |
| 70 | 7.8 | Zirconia Z-1044 | 0.8 | 3.2 | 100 | 40 |
| 71 | 8.1 | Zirconia Z-1044 | 1.2 | 2.8 | 100 | 44 |
| 72 | 7.8 | Zirconia Z-1044 | 1.6 | 2.4 | 100 | 36 |
| 73 | 8.2 | Zirconia Z-1044 | 2.0 | 2.0 | 100 | 36 |
| 74 | 8.0 | Zirconia Z-1044 | 2.4 | 1.6 | 100 | 32 |
| 75 | 7.5 | Zirconia Z-1044 | 2.4 | 5.6 | 100 | 58 |
| 76 | 8.1 | Zirconia Z-1044 | 2.8 | 1.2 | 100 | 26 |
| 77 | 7.9 | Zirconia Z-1044 | 3.2 | 0.8 | 100 | 19 |
| 78 | 7.9 | Zirconia Z-1044 | 3.2 | 4.8 | 100 | 58 |
| 79 | 8.0 | Zirconia Z-1044 | 3.6 | 0.4 | 100 | 7 |
| 80 | 8.5 | Zirconia Z-1044 | 4.0 | 0.0 | 100 | 3 |
| 81 | 8.0 | Zirconia Z-1044 | 4.0 | 4.0 | 100 | 57 |
| 82 | 8.0 | Zirconia Z-1044 | 4.8 | 3.2 | 100 | 47 |
| 83 | 7.6 | Zirconia Z-1044 | 5.6 | 2.4 | 100 | 31 |
| 84 | 7.7 | Zirconia Z-1044 | 6.4 | 1.6 | 100 | 16 |

Example 2

88 µA of an aqueous solution of HAuCl$_4$ (containing 0.2254 wt % gold) was added to a suspension of 10 mg titania (P25, Acros Organics) in deionized water (550 µA) while shaking. The suspension was shaken at room temperature for 30 min. 250 µl of an aqueous solution of NH$_4$OH (4.0 M) was added to above suspension and the resulting suspension was shaken at room temperature for 2 hours. The suspension was then centrifuged and supernatant was decanted. After residual liquid was removed using filter paper, the light yellow solid was dried in a 60° C. oven overnight under a dry air purge.

Another batch of material was prepared by repeating above preparation with exception that after the light yellow solid was collected, it was washed with deionized water (2 times of 500 µl each) before it was dried in a 60° C. oven overnight under a dry air purge.

2.1 µl of an aqueous solution of Pt(NO$_3$)$_2$ (containing 7.7 wt % platinum) was added to the above solids and the mixtures were agitated to impregnate the gold-containing supports. The samples were dried in a 60° C. oven overnight under a dry air purge. The samples were then reduced at 350° C. under forming gas (5% H$_2$ and 95% N$_2$) atmosphere for 3 hours with 2° C./min temperature ramp rate. The final catalysts contained approximately 2.0 wt % gold and 2.0 wt % platinum.

By adjusting the volume and concentration of solutions of HAuCl$_4$, NH$_4$OH, and Pt(NO$_3$)$_2$, a series of other catalysts with various loadings of gold (2 or 4 wt %) and platinum (2 or 4 wt %) were prepared using the Zirconia Z-1628 (Daiichi Kigenso Kagaku Kogyo), Silica-Titania Cariact (Fuji Silysia) and Silica Cariact Q-10 (Fuji Silysia).

These catalysts were tested for glucose oxidation using Catalyst testing protocol 1 and results are summarized in Table 2.

cooled to room temperature, centrifuged and supernatant was decanted. After residual liquid was removed using filter paper, the light yellow solid was dried in a 60° C. oven overnight under a dry air purge.

Another batch of material was prepared by repeating above preparation with exception that after the light yellow solid was collected, it was washed with deionized water (2 times of 2000 µl each) before it was dried in a 60° C. oven overnight under a dry air purge.

2.1 µl of an aqueous solution of Pt(NO$_3$)$_2$ (containing 7.7 wt % platinum) was added to above solid and the mixture was agitated to impregnate the gold-containing support. The sample was dried in a 60° C. oven overnight under a dry air purge. The sample was then reduced at 350° C. under forming gas (5% H$_2$ and 95% N$_2$) atmosphere for 3 hours with 2° C./min temperature ramp rate. The final catalyst contained approximately 2.0 wt % gold and 2.0 wt % platinum.

TABLE 2

Conditions and results of glucose oxidation on gold/platinum catalysts of Example 2

| Entry | Catalyst Amount (mg) | Support | Au wt % | Pt wt % | Wash after Au deposition | Glucose Conversion (%) | Glucaric Acid Yield (%) |
|---|---|---|---|---|---|---|---|
| 4 | 7.0 | Silica Cariact Q-10 | 2 | 2 | No | 100 | 28 |
| 5 | 7.2 | Silica Cariact Q-10 | 2 | 2 | Yes | 100 | 28 |
| 7 | 7.1 | Silica Cariact Q-10 | 4 | 4 | Yes | 100 | 48 |
| 8 | 8.0 | Silica Cariact Q-10 | 4 | 4 | No | 100 | 44 |
| 21 | 7.1 | Titania ST 31119 | 4 | 4 | No | 100 | 62 |
| 23 | 7.4 | Titania-Silica Cariact | 4 | 4 | Yes | 100 | 39 |
| 24 | 7.4 | Titania-Silica Cariact | 4 | 4 | No | 100 | 41 |
| 29 | 6.6 | Zirconia 1628 | 2 | 2 | Yes | 100 | 26 |
| 30 | 6.6 | Zirconia 1628 | 2 | 2 | No | 100 | 22 |

Example 3

88 µl of an aqueous solution of HAuCl$_4$ (containing 0.2254 wt % gold) was added to a suspension of 10 mg titania (P25, Acros Organics) in deionized water (1900 µl) while shaking. The suspension (at concentration of 5 mg support/ml) was shaken at room temperature for 30 min. 400 µl of an aqueous solution of urea (20 wt %) was added to above suspension and the resulting suspension was heated at 80° C. for 2 hours while shaking. The suspension was then Similar method was also used to prepare catalysts based on other supports, including Zirconia Z-1628 (Daiichi Kigenso Kagaku Kogyo), Zirconia Z-1044 (Daiichi Kigenso Kagaku Kogyo), Silica-Titania Cariact (Fuji Silysia) and Silica Cariact Q-10 (Fuji Silysia).

These catalysts were tested for glucose oxidation using Catalyst testing protocol 1 and results are summarized in Table 3.

TABLE 3

Conditions and results of glucose oxidation on gold/platinum catalysts of Example 3

| Entry | Support | Wash after Au deposition | Concentration of Suspension (mg support/ml) | Catalyst Amount (mg) | Glucose Conversion (%) | Glucaric Acid Yield (%) |
|---|---|---|---|---|---|---|
| 1 | Silica Cariact Q-10 | No | 5 | 9.2 | 100 | 23 |
| 2 | Silica Cariact Q-10 | Yes | 5 | 7.0 | 100 | 17 |
| 3 | Silica-Titania | No | 5 | 8.8 | 100 | 30 |
| 4 | Silica-Titania | Yes | 5 | 8.4 | 100 | 34 |
| 5 | Titania P25 | No | 5 | 7.4 | 100 | 35 |
| 6 | Titania P25 | Yes | 5 | 7.0 | 100 | 37 |
| 7 | Zirconia 1628 | No | 5 | 7.4 | 80 | 11 |
| 8 | Zirconia 1628 | Yes | 5 | 7.7 | 100 | 22 |
| 9 | Zirconia Z-1044 | No | 5 | 7.8 | 100 | 22 |
| 10 | Zirconia Z-1044 | Yes | 5 | 7.2 | 100 | 26 |

Example 4

12 μl of an aqueous solution of HAuCl$_4$ (containing 22.54 wt % gold) was added to a suspension of 187 mg Silica Cariact Q-10 (Fuji Silysia) in deionized water (38 ml) while stirring. The suspension was stirred at room temperature for 30 min. 100 μl of an aqueous solution of NH$_4$OH (15.85 M) was added to above suspension and the resulting suspension was stirred at room temperature for 2 hours. The suspension was then centrifuged and supernatant was decanted. The light yellow solid was washed with deionized water (2 times of 35 ml each) at 50° C. before it was dried in a 60° C. oven overnight under a dry air purge. The sample was then reduced at 200° C. under forming gas (5% H$_2$ and 95% N$_2$) atmosphere for 3 hours with 2° C./min temperature ramp rate.

10 mg of dry material from above preparation was used for the following synthesis.

12.8 μA of an aqueous solution of Pt(NO$_3$)$_2$ (containing 1.5 wt % platinum) was added to above solid (10 mg) and the mixture was agitated to impregnate the gold-containing support. The sample was dried in a 60° C. oven overnight under a dry air purge. The sample was then reduced at 350° C. under forming gas (5% H$_2$ and 95% N$_2$) atmosphere for 3 hours with 2° C./min temperature ramp rate. The final catalyst contained approximately 2.0 wt % gold and 2.0 wt % platinum.

The catalyst was tested for glucose oxidation using Catalyst testing protocol 1 and results are summarized in Table 4.

TABLE 4

Conditions and results of glucose oxidation on gold/platinum catalysts of Example 4

| Entry | Support | Catalyst Amount (mg) | Glucose Conversion (%) | Glucaric Acid Yield (%) |
|---|---|---|---|---|
| 1 | Silica Cariact Q-10 | 8.3 | 100 | 48 |

Example 5

12 μl of an aqueous solution of HAuCl$_4$ (containing 22.54 wt % gold) was added to a suspension of 187 mg Silica Cariact Q-10 (Fuji Silysia) in deionized water (38 ml) while stirring. The suspension was stirred at room temperature for 30 min. 100 μl of an aqueous solution of NH$_4$OH (15.85 M) was added to above suspension and the resulting suspension was stirred at room temperature for 2 hours. The suspension was then centrifuged and supernatant was decanted. The light yellow solid was washed with deionized water (2 times of 35 ml each) at 50° C. before it was dried in a 60° C. oven overnight under a dry air purge. The sample was then reduced at 200° C. under forming gas (5% H$_2$ and 95% N$_2$) atmosphere for 3 hours with 2° C./min temperature ramp rate.

10 mg of dry material from above preparation was used for the following synthesis.

12.8 μl of an aqueous solution of Pt(NO$_3$)$_2$ (containing 1.5 wt % platinum) was added to above solid (10 mg) and the mixture was agitated to impregnate the gold-containing support. The sample was dried in a 60° C. oven overnight under a dry air purge. The sample was calcined at 350° C. in air for 3 hours with 5° C./min temperature ramp rate, then reduced at 350° C. under forming gas (5% H$_2$ and 95% N$_2$) atmosphere for 3 hours with 2° C./min temperature ramp rate. The final catalyst contained approximately 2.0 wt % gold and 2.0 wt % platinum.

The catalyst was tested for glucose oxidation using Catalyst testing protocol 1 and results are summarized in Table 5.

TABLE 5

Conditions and results of glucose oxidation on gold/platinum catalysts of Example 5

| Entry | Support | Catalyst Amount (mg) | Glucose Conversion (%) | Glucaric Acid Yield (%) |
|---|---|---|---|---|
| 1 | Silica Cariact Q-10 | 8.7 | 100 | 43 |

Example 6

12 μl of an aqueous solution of HAuCl$_4$ (containing 22.54 wt % gold) was added to a suspension of 187 mg Silica Cariact Q-10 (Fuji Silysia) in deionized water (38 ml) while stirring. The suspension was stirred at room temperature for 30 min. 100 μl of an aqueous solution of NH$_4$OH (15.85 M) was added to above suspension and the resulting suspension was stirred at room temperature for 2 hours. The suspension was then centrifuged and supernatant was decanted. The light yellow solid was washed with deionized water (2 times of 35 ml each) at 50° C. before it was dried in a 60° C. oven overnight under a dry air purge. The sample was then calcined at 350° C. in air for 3 hours with 5° C./min temperature ramp rate.

10 mg of dry material from above preparation was used for the following synthesis.

12.8 μl of an aqueous solution of Pt(NO$_3$)$_2$ (containing 1.5 wt % platinum) was added to above solid (10 mg) and the mixture was agitated to impregnate the gold-containing support. The sample was dried in a 60° C. oven overnight under a dry air purge. The sample was then reduced at 350° C. under forming gas (5% H$_2$ and 95% N$_2$) atmosphere for 3 hours with 2° C./min temperature ramp rate. The final catalyst contained approximately 2.0 wt % gold and 2.0 wt % platinum.

The catalyst was tested for glucose oxidation using Catalyst testing protocol 1 and results are summarized in Table 6.

TABLE 6

Conditions and results of glucose oxidation on gold/platinum catalysts of Example 6

| Entry | Support | Catalyst Amount (mg) | Glucose Conversion (%) | Glucaric Acid Yield (%) |
|---|---|---|---|---|
| 1 | Silica Cariact Q-10 | 8.4 | 100 | 42 |

Example 7

625 μl of an aqueous solution of HAuCl$_4$ (containing 22.54 wt % gold) was added to a suspension of 5.0 g titania (P25, Acros Organics) in deionized water (500 ml) while stirring. The suspension was stirred at room temperature for 30 min. 30 ml of an aqueous solution of urea (20 wt %) was added to above suspension and the resulting suspension was heated at 80° C. for overnight while stirring. The suspension was then cooled to room temperature, centrifuged and supernatant was decanted. The light yellow solid was washed with deionized water (3 times of 400 ml each) at 50° C. before it was dried in a 60° C. oven overnight under a dry air purge. The sample was then reduced at 200° C. under forming gas (5% $H_2$ and 95% $N_2$) atmosphere for 3 hours with 2° C./min temperature ramp rate to give 4.90 g purple solid.

1.225 ml of an aqueous solution of $Pt(NO_3)_2$ (containing 11.4 wt % platinum) was added to the above purple solid in 4 portions. After each addition, the mixture was agitated to impregnate the gold-containing support. The sample was dried in a 60° C. oven overnight under a dry air purge. The sample was then reduced at 350° C. under forming gas (5% $H_2$ and 95% $N_2$) atmosphere for 3 hours with 2° C./min temperature ramp rate. The final catalyst contained approximately 4.0 wt % gold and 4.0 wt % platinum.

The catalyst was tested for glucose oxidation using Catalyst testing protocol 2 and results are summarized in Table 7.

TABLE 7

Conditions and results of glucose oxidation on gold/platinum catalyst of Example 7

| Entry | Temperature (° C.) | Reaction Time (h) | Glucose Conversion (%) | Glucaric Acid Yield (%) |
|---|---|---|---|---|
| 1 | 91 | 3.0 | 100 | 42 |
| 2 | 91 | 5.0 | 100 | 50 |
| 3 | 98 | 3.0 | 100 | 49 |
| 4 | 98 | 5.0 | 100 | 59 |
| 5 | 105 | 3.0 | 100 | 59 |
| 6 | 105 | 5.0 | 100 | 67 |
| 7 | 112 | 3.0 | 100 | 67 |
| 8 | 112 | 5.0 | 100 | 70 |
| 9 | 119 | 2.0 | 100 | 66 |
| 10 | 133 | 1.0 | 100 | 65 |

Example 8

Method similar to that in Example 7 was used to prepare catalyst based on titania (ST 31119, Saint-Gobain Norpro).

This catalyst was tested for glucose oxidation using Catalyst testing protocol 2 and results are summarized in Table 8.

TABLE 8

Conditions and results of glucose oxidation on gold/platinum catalyst of Example 8

| Entry | Temperature (° C.) | Reaction Time (h) | Glucose Conversion (%) | Glucaric Acid Yield (%) |
|---|---|---|---|---|
| 1 | 91 | 5.0 | 100 | 51 |
| 2 | 98 | 3.0 | 100 | 52 |
| 3 | 98 | 5.0 | 100 | 59 |
| 4 | 105 | 3.0 | 100 | 58 |
| 5 | 112 | 3.0 | 100 | 68 |
| 6 | 119 | 2.0 | 100 | 69 |
| 7 | 119 | 3.0 | 100 | 71 |
| 8 | 126 | 2.0 | 100 | 70 |

Example 9

312 µl of an aqueous solution of $HAuCl_4$ (containing 22.54 wt % gold) was added to a suspension of 5.0 g titania (P25, Acros Organics) in deionized water (500 ml) while stirring. The suspension was stirred at room temperature for 30 min. 15 ml of an aqueous solution of urea (20 wt %) was added to above suspension and the resulting suspension was heated at 80° C. for overnight while stirring. The suspension was then cooled to room temperature, centrifuged and supernatant was decanted. The light yellow solid was washed with deionized water (3 times of 400 ml each) at 50° C. before it was dried in a 60° C. oven overnight under a dry air purge. The sample was then reduced at 200° C. under forming gas (5% $H_2$ and 95% $N_2$) atmosphere for 3 hours with 2° C./min temperature ramp rate to give 4.90 g purple solid.

612 µA of an aqueous solution of $Pt(NO_3)_2$ (containing 11.4 wt % platinum) was added to above purple solid in 4 portions. After each addition, the mixture was agitated to impregnate the gold-containing support. The sample was dried in a 60° C. oven overnight under a dry air purge. The sample was then reduced at 350° C. under forming gas (5% $H_2$ and 95% $N_2$) atmosphere for 3 hours with 2° C./min temperature ramp rate. The final catalyst contained approximately 2.0 wt % gold and 2.0 wt % platinum.

This catalyst was tested for glucose oxidation using Catalyst testing protocol 2 and results are summarized in Table 9.

TABLE 9

Conditions and results of glucose oxidation on gold/platinum catalyst of Example 9

| Entry | Temperature (° C.) | Reaction time (h) | Substrate Glucose wt % | Glucose Conversion (%) | Glucaric Acid Yield (%) |
|---|---|---|---|---|---|
| 1 | 90 | 5.0 | 10 | 100 | 32 |
| 2 | 90 | 3.0 | 10 | 100 | 26 |
| 3 | 90 | 5.0 | 20 | 100 | 21 |

Example 10

88 µl of an aqueous solution of $HAuCl_4$ (containing 0.2254 wt % gold) was added to a suspension of 10 mg titania (ST 31119, Saint-Gobain Norpro) in deionized water (450 µl) while shaking. The suspension was shaken at room temperature for 30 min. 250 µl of an aqueous solution of $NH_4OH$ (4.0 M) was added to above suspension and the resulting suspension was shaken at room temperature for 2 hours. The suspension was then centrifuged and supernatant was decanted. After residual liquid was removed using filter paper, the light yellow solid was dried in a 60° C. oven overnight under a dry air purge.

2.1 µl of an aqueous solution of $(NH_3)_4Pt(NO_3)_2$ (containing 7.7 wt % platinum) was added to above solid and the mixture was agitated to impregnate the gold-containing support. The sample was dried in a 60° C. oven overnight under a dry air purge. The sample was then reduced at 350° C. under forming gas (5% $H_2$ and 95% $N_2$) atmosphere for 3 hours with 2° C./min temperature ramp rate. The final catalyst contained approximately 2.0 wt % gold and 2.0 wt % platinum.

By adjusting the volume and concentration of solutions of $HAuCl_4$, $NH_4OH$, and $(NH_3)_4Pt(NO_3)_2$, a series of other catalysts with various loadings of gold (0 to 2 wt %) and platinum (0 to 2 wt %) were prepared. Similar method was also used to prepare catalysts based on Zirconia Z-1044 (Daiichi Kigenso Kagaku Kogyo). These catalysts were tested for glucose oxidation using Catalyst testing protocol 1 and results are summarized in Table 10.

TABLE 10

Conditions and results of glucose oxidation on gold/platinum catalyst of Example 10

| Entry | Catalyst Amount (mg) | Support | Au wt % | Pt wt % | Glucose Conversion (%) | Glucaric Acid Yield (%) |
|---|---|---|---|---|---|---|
| 1 | 8.8 | Titania ST 31119 | 1.4 | 2.6 | 100 | 28 |
| 2 | 8.6 | Titania ST 31119 | 2.0 | 2.0 | 100 | 30 |
| 3 | 9 | Zirconia Z-1044 | 1.4 | 2.6 | 100 | 35 |
| 4 | 8.6 | Zirconia Z-1044 | 2.0 | 2.0 | 100 | 17 |

Example 11

2.1 μl of an aqueous solution of $Pt(NO_3)_2$ (containing 7.7 wt % platinum) was added to 10 mg titania (ST 31119, Saint-Gobain Norpro) and the mixture was agitated to impregnate the support. The sample was dried in a 60° C. oven overnight under a dry air purge. The sample was then reduced at 350° C. under forming gas (5% $H_2$ and 95% $N_2$) atmosphere for 3 hours with 2° C./min temperature ramp rate.

88 μl of an aqueous solution of $HAuCl_4$ (containing 0.2254 wt % gold) was added to a suspension of above solid in deionized water (550 μl) while shaking. The suspension was shaken at room temperature for 30 min. 250 μl of an aqueous solution of $NH_4OH$ (4.0 M) was added to above suspension and the resulting suspension was shaken at room temperature for 2 hours. The suspension was then centrifuged and supernatant was decanted. After residual liquid was removed using filter paper, the solid was collected and dried in a 60° C. oven overnight under a dry air purge. The sample was then reduced at 350° C. under forming gas (5% $H_2$ and 95% $N_2$) atmosphere for 3 hours with 2° C./min temperature ramp rate. The final catalyst contained approximately 2.0 wt % gold and 2.0 wt % platinum.

By adjusting the volume and concentration of solutions of $HAuCl_4$, $NH_4OH$, and $Pt(NO_3)_2$, a series of other catalysts with various loadings of gold (0.4 to 2 wt %) and platinum (1.0 to 3.2 wt %) were prepared. Similar method was also used to prepare catalysts based on Zirconia Z-1044 (Daiichi Kigenso Kagaku Kogyo). These catalysts were tested for glucose oxidation using Catalyst testing protocol 1 and results are summarized in Table 11.

Example 12

2.1 μl of an aqueous solution of $Pt(NO_3)_2$ (containing 7.7 wt % platinum) was added to 10 mg titania (ST 31119, Saint-Gobain Norpro) and the mixture was agitated to impregnate the support. The sample was dried in a 60° C. oven overnight under a dry air purge. The sample was then calcined at 500° C. in air for 3 hours with 5° C./min temperature ramp rate.

88 μl of an aqueous solution of $HAuCl_4$ (containing 0.2254 wt % gold) was added to a suspension of above solid in deionized water (550 μl) while shaking. The suspension was shaken at room temperature for 30 min. 250 μl of an aqueous solution of $NH_4OH$ (4.0 M) was added to above suspension and the resulting suspension was shaken at room temperature for 2 hours. The suspension was then centrifuged and supernatant was decanted. After residual liquid was removed using filter paper, the solid was dried in a 60° C. oven overnight under a dry air purge. The sample was then reduced at 350° C. under forming gas (5% $H_2$ and 95% $N_2$) atmosphere for 3 hours with 2° C./min temperature ramp rate. The final catalyst contained approximately 2.0 wt % gold and 2.0 wt % platinum.

By adjusting the volume and concentration of solutions of $HAuCl_4$, $NH_4OH$, and $Pt(NO_3)_2$, a series of other catalysts with various loadings of gold (0 to 2 wt %) and platinum (0 to 2 wt %) were prepared. Similar method was also used to prepare catalysts based on Zirconia Z-1044 (Daiichi Kigenso Kagaku Kogyo). These catalysts were tested for glucose oxidation using Catalyst testing protocol 1 and results are summarized in Table 12.

TABLE 11

Conditions and results of glucose oxidation on gold/platinum catalyst of Example 11

| Entry | Catalyst Amount (mg) | Support | Au wt % | Pt wt % | Glucose Conversion (%) | Glucaric Acid Yield (%) |
|---|---|---|---|---|---|---|
| 1 | 8.2 | Titania ST 31119 | 0.4 | 1.6 | 72 | 15 |
| 2 | 8.7 | Titania ST 31119 | 0.7 | 1.3 | 100 | 25 |
| 3 | 8.2 | Titania ST 31119 | 0.8 | 3.2 | 93 | 30 |
| 4 | 7.9 | Titania ST 31119 | 1.0 | 1.0 | 100 | 21 |
| 5 | 8.9 | Titania ST 31119 | 1.4 | 2.6 | 100 | 43 |
| 6 | 8.8 | Titania ST 31119 | 2.0 | 2.0 | 100 | 43 |
| 7 | 7.9 | Zirconia Z-1044 | 0.4 | 1.6 | 72 | 11 |
| 8 | 7.9 | Zirconia Z-1044 | 0.7 | 1.3 | 100 | 27 |
| 9 | 8.4 | Zirconia Z-1044 | 0.8 | 3.2 | 97 | 33 |
| 10 | 7.3 | Zirconia Z-1044 | 1.0 | 1.0 | 100 | 27 |
| 11 | 8 | Zirconia Z-1044 | 1.4 | 2.6 | 100 | 47 |
| 12 | 8.3 | Zirconia Z-1044 | 2.0 | 2.0 | 100 | 42 |

TABLE 12

Conditions and results of glucose oxidation on gold/platinum catalyst of Example 12

| Entry | Catalyst Amount (mg) | Support | Au wt % | Pt wt % | Glucose Conversion (%) | Glucaric Acid Yield (%) |
|---|---|---|---|---|---|---|
| 1 | 7.9 | Titania ST 31119 | 0.4 | 1.6 | 85 | 17 |
| 2 | 8.1 | Titania ST 31119 | 0.7 | 1.3 | 100 | 28 |
| 3 | 7.9 | Titania ST 31119 | 0.8 | 3.2 | 100 | 44 |
| 4 | 8.2 | Titania ST 31119 | 1.0 | 1.0 | 100 | 21 |
| 5 | 7.7 | Titania ST 31119 | 1.4 | 2.6 | 100 | 49 |
| 6 | 8.2 | Titania ST 31119 | 2.0 | 2.0 | 100 | 43 |
| 7 | 7.8 | Zirconia Z-1044 | 0.4 | 1.6 | 99 | 23 |
| 8 | 8.2 | Zirconia Z-1044 | 0.7 | 1.3 | 100 | 30 |
| 9 | 7.7 | Zirconia Z-1044 | 0.8 | 3.2 | 100 | 46 |
| 10 | 7.9 | Zirconia Z-1044 | 1.0 | 1.0 | 100 | 27 |
| 11 | 9.2 | Zirconia Z-1044 | 1.4 | 2.6 | 100 | 51 |
| 12 | 8.5 | Zirconia Z-1044 | 2.0 | 2.0 | 100 | 40 |

Example 13

Preparation of Platinum/Gold Catalyst from Au/TiO2 [Sud Chemie 02-10]

$Pt(NO_3)_2$ solution was added to a dried sample of the commercial 1.5% gold/titania catalyst [Süd Chemie 02-10] (wherein the total volume of the $Pt(NO_3)_2$ volume was matched to equal to the pore volume of the catalyst) with agitation, whereupon the material was dried in a furnace at 120° C. for 1 hour, followed by reduction under flowing 5 vol. % $H_2$ in $N_2$ at 350° C. for 3 hours. The results are presented as Entry 1 of Table 13.

Preparation of 4 Wt % Platinum/4 Wt % Gold Catalyst

Pt(NO3)2 solution and $AuCl_2$ solution was added to a dried sample of Titania NorPro ST 61120 (Saint Gobain Norpro) with agitation, whereupon the material was dried in a furnace at 120° C. for 16 hours. A Pt(NO3)2 solution was subsequently added to the dried sample of Au/Titania N or Pro ST 61120 with agitation, whereupon the material was dried in a furnace at 120° C. for 16 hours followed by a reduction at 350° C. under flowing 5 vol. % $H_2$ in $N_2$ for 3 hours. The results are presented as Entry 2 of Table 13.

TABLE 13

| Entry | Catalyst (wt. % M2 wt. % Pt/Support) | M1 Precursor | M2 Precursor | Temp. (° C.) | Time (Hours) | Catalyst Amount (mg) | Glucaric Acid Yield (%) |
|---|---|---|---|---|---|---|---|
| 1 | 1.5% Pt 1.5% Au/Titania [Süd Chemie 02-10] | — | $Pt(NO_3)_2$ | 100 | 5 | 8 | 55 |
| 2 | 4% Pt 4% Au/Titania NorPro ST 61120 | $HAuCl_2$ | $Pt(NO_3)_2$ | 100 | 5 | 8 | 32 |

What is claimed is:

1. A catalyst composition comprising particles of gold-platinum alloy and particles consisting essentially of platinum (0) on a support comprising titania wherein (a) the molar ratio of platinum to gold of the catalyst is from about 4:1 to 1:1, (b) the particle sizes of the platinum (0) particles are substantially in the range of from about 2 to about 50 nanometers, (c) the total gold and platinum metal loading of the catalyst is from about 2 to about 8 wt %, and (d) the gold-platinum alloy is formed at a temperature between about 200° C. and about 350° C. and wherein the catalyst has the ability to catalyze conversion of glucose to glucaric acid at a yield in excess of 60%.

2. The catalyst composition of claim 1 wherein the total gold and platinum metal loading of the catalyst is from about 2 to about 4 wt %.

3. The catalyst composition of claim 2 wherein the molar ratio of platinum to gold of the catalyst is from about 3:1 to 1:1.

4. The catalyst composition of claim 2 wherein the molar ratio of platinum to gold of the catalyst is from about 2:1 to 1:1.

5. The catalyst composition of claim 1 wherein the particles sizes of the particles consisting essentially of platinum (0) are substantially in the range of from about 5 to about 20 nanometers.

6. The catalyst composition of claim 1 wherein the particle sizes of the gold-platinum alloy particles are substantially in the range of from about 2 to about 20 nanometers.

7. The catalyst composition of claim 6 wherein at least about 50% of the gold-platinum alloy particles have a size from about 5 to about 12 nanometers.

8. The catalyst composition of claim 6 wherein the total gold and platinum metal loading of the catalyst is from about 2 to about 4 wt %.

9. The catalyst composition of claim 8 wherein the molar ratio of platinum to gold of the catalyst is from about 3:1 to 1:1.

10. The catalyst composition of claim 8 wherein the molar ratio of platinum to gold of the catalyst is from about 2:1 to 1:1.

11. The catalyst composition of claim 1 wherein at least about 50% of the particles consisting essentially of platinum (0) have a size from about 8 to about 12 nanometers.

12. The catalyst composition of claim 1 wherein the molar ratio of platinum to gold of the catalyst is from about 3:1 to 1:1.

13. The catalyst composition of claim 1 wherein the molar ratio of platinum to gold of the catalyst is from about 2:1 to 1:1.

14. The catalyst composition of claim 1 further comprising metal selected from Group 6 metals.

15. The catalyst composition of claim 1 further comprising a Group 10 metal in addition to platinum.

16. A process for preparing glucaric acid or derivatives thereof comprising reacting glucose with a source of oxygen in the presence of the catalyst of claim 1.

17. The process of claim 16 wherein the particle sizes of the gold-platinum alloy particles are substantially in the range of from about 2 to about 20 nanometers.

18. The process of claim 17 wherein the total gold and platinum metal loading of the catalyst is from about 2 to about 4 wt %.

19. The process of claim 16 wherein the total gold and platinum metal loading of the catalyst is from about2 to about 4 wt %.

20. The process of claim 16 wherein the catalyst further comprises a metal selected from Group 6 metals.

21. The process of claim 16 wherein the catalyst further comprises a Group 10 metal in addition to platinum.

22. The process of claim 16 wherein the catalyst further comprises wherein the molar ratio of platinum to gold of the catalyst is from about 2:1 to 1:1.

* * * * *